United States Patent
Carceller Gonzalez et al.

(10) Patent No.: US 8,901,146 B2
(45) Date of Patent: Dec. 2, 2014

(54) AMINOALKYLPYRIMIDINE DERIVATIVES AS HISTAMINE H4 RECEPTOR ANTAGONISTS

(75) Inventors: Elena Carceller Gonzalez, Sant Cugat del Vallé (ES); Marina Virgili Bernado, Barcelona (ES); Robert Soliva Soliva, Sant Fellu De Llobregat (ES); Carles Ferrer Costa, Calella (ES)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 12 days.

(21) Appl. No.: 13/518,729
(22) PCT Filed: Dec. 22, 2010
(86) PCT No.: PCT/EP2010/070562
§ 371 (c)(1),
(2), (4) Date: Oct. 1, 2012
(87) PCT Pub. No.: WO2011/076878
PCT Pub. Date: Jun. 30, 2011

(65) Prior Publication Data
US 2013/0018031 A1 Jan. 17, 2013

Related U.S. Application Data

(60) Provisional application No. 61/307,579, filed on Feb. 24, 2010.

(30) Foreign Application Priority Data

Dec. 23, 2009 (EP) ..................... 09382302

(51) Int. Cl.
| | | |
|---|---|---|
| A01N 43/54 | (2006.01) | |
| A61K 31/505 | (2006.01) | |
| C07D 403/04 | (2006.01) | |
| C07D 401/14 | (2006.01) | |
| C07D 403/14 | (2006.01) | |
| C07D 409/14 | (2006.01) | |
| C07D 239/48 | (2006.01) | |
| A61K 31/506 | (2006.01) | |

(52) U.S. Cl.
CPC ............. *C07D 403/04* (2013.01); *A61K 31/505* (2013.01); *C07D 239/48* (2013.01); *A61K 31/506* (2013.01); *C07D 401/14* (2013.01); *C07D 403/14* (2013.01); *C07D 409/14* (2013.01)
USPC ............. 514/275; 544/323; 544/324

(58) Field of Classification Search
CPC ............. A61K 31/505; C07D 239/48
USPC ............. 544/324, 323; 514/275
See application file for complete search history.

(56) References Cited

U.S. PATENT DOCUMENTS

| | | | |
|---|---|---|---|
| 6,716,978 B2 * | 4/2004 | Marfat | 540/575 |
| 7,494,987 B2 * | 2/2009 | Akada et al. | 514/210.01 |
| 7,528,143 B2 * | 5/2009 | Noronha et al. | 514/275 |
| 7,737,153 B2 | 6/2010 | Feurer et al. | |

FOREIGN PATENT DOCUMENTS

| | | |
|---|---|---|
| EP | 1505064 | 2/2005 |
| WO | 2004/039796 | 5/2004 |
| WO | 2005/054239 | 6/2005 |
| WO | 2006/110763 | 10/2006 |
| WO | 2007/031529 | 3/2007 |
| WO | 2007/072163 | 6/2007 |
| WO | 2008/031556 | 3/2008 |
| WO | 2008/060766 | 5/2008 |
| WO | 2008/100565 | 8/2008 |
| WO | 2009/068512 | 6/2009 |
| WO | 2009/077608 | 6/2009 |
| WO | 2009/080721 | 7/2009 |

OTHER PUBLICATIONS

I. Collins, Current Signal Transduction Therapy, 1, 13-23, 13 (2006).*
Y.S. Yoon et al., 9 The International Journal of Tuberculosis and Lung Disease, 1215-1219 (2005).*
J.D. Henderer et al., Ocular Pharmacology, in Goodman & Gilman's the Pharmacological Basis of Therapeutics 1679-1737 (L, Burnton et al. eds., 11th ed., 2006).*
P.K. Buxton, ABC of Dermatology [e-book] (4th ed., BMJ Books, 2003).*
L.P. Fox et al., Dermatological Pharmacology, in Goodman & Gilman's the Pharmacological Basis of Therapeutics 1679-1705 (L, Burnton et al. eds., 11th ed., 2006).*
S.K. Bhatia et al., Autoimmunity and autoimmune disease in 6 Principles of Medical Biology 239-263, 244 (1996).*
J-U Peters et al., 14 Bioorganic & Medicinal Chemistry Letters, 3575-3578 (2004).*
S.M. Hayter et al., Autoimmunity Reviews, 754-765, 756 (2012).*
M. Meriggioli et al. The Lancet Neurology 475-490 (2009).*
J.H. Poupaert, Drug Design: Basic Principles and Applications, in 2 Encyclopedia of Pharmaceutical Technology 1362-1369, 1367 (James Swarbrick ed., 3rd ed., 2007).*

(Continued)

*Primary Examiner* — James O. Wilson
*Assistant Examiner* — Alexander R Pagano
(74) *Attorney, Agent, or Firm* — Kilpatrick Townsend & Stockton LLP

(57) ABSTRACT

Aminoalkylpyrimidine derivatives of formula I, wherein the meaning of the different substituents are those indicated in the description. These compounds are useful as histamine $H_4$ receptor antagonists.

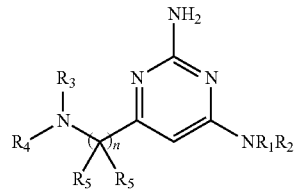

21 Claims, No Drawings

(56) References Cited

OTHER PUBLICATIONS

L.I. Zon et al., Nature Reviews Drug Discovery 4, 35 (2005).*

G. M Cleator et al., Herpes Simplex in, Principles and Practice of Clinical Virology 27-51, 44 (Arie J. Zuckerman et al., eds., 5th ed., 2004).*

E. Zampeli et al., 157 British Journal of Pharmacology, 24-33 (2009).*

Dijkstra et al., 128 Journal of Investigative Dermatology, 1696-1703 (2008).*

J-F. Huang et al., 8 Current Allergy and Asthma Reports, 21-27 (2008).*

R.L. Thurmond et al., 7 Nature Reviews Drug Discovery, 41-53 (2008).*

M. Zhang et al., 15 Expert Opinion on Investigational Drugs, 1443-1452 (2006).*

A.R. Ahmed et al., 355 New England Journal of Medicine, 1772-1779 (2006).*

Thurmond et al., 309 The Journal of Pharmacology and Experimental Therapeutics, 404-413 (2004).*

C. Abad-Zapatero, Drug Discovery Today, 1-8 (2010).*

Cowart et al., "Rotationally Constrained 2,4-Diamino-5,6-disubstituted Pyrimidines: A New Class of Histamine H4 Receptor Antagonists with Improved Druglikeness and in Vivo Efficacy in Pain and Inflammation Models," Journal of Medicinal Chemistry (Sep. 26, 2008): vol. 51, pp. 6547-6557.

* cited by examiner

AMINOALKYLPYRIMIDINE DERIVATIVES AS HISTAMINE H4 RECEPTOR ANTAGONISTS

CROSS-REFERENCE TO RELATED APPLICATIONS

This application is a U.S. National Phase Application and claims the priority of International Application No. PCT/EP10/070,562 filed Dec. 22, 2010, which claims priority to EP Application No. 09382302.9 filed Dec. 23, 2009 and U.S. Provisional Application No. 61/307,579 filed Feb. 24, 2010, the disclosure of which are hereby incorporated by reference in their entirety.

FIELD OF THE INVENTION

The present invention relates to a new series of aminoalkylpyrimidine derivatives, processes to prepare them, pharmaceutical compositions comprising these compounds as well as their use in therapy.

BACKGROUND OF THE INVENTION

Histamine is one of the most potent mediators of immediate hypersensitivity reactions. While the effects of histamine on smooth muscle cell contraction, vascular permeability and gastric acid secretion are well known, its effects on the immune system are only now beginning to become unveiled.

A few years ago, a novel histamine receptor, which was named $H_4$, was cloned by several research groups working independently (Oda T et al, *J Biol Chem* 2000, 275: 36781-6; Nguyen T of al, *Mol Pharmacol* 2001, 59: 427-33). As the other members of its family, it is a G-protein coupled receptor (GPCR) containing 7 transmembrane segments. However, the $H_4$ receptor has low homology with the three other histamine receptors (Oda T of al); it is remarkable that it shares only a 35% homology with the $H_3$ receptor. While the expression of the $H_3$ receptor is restricted to cells of the central nervous system, the expression of the $H_4$ receptor has been mainly observed in cells of the haematopoietic lineage, in particular eosinophils, mast cells, basophils, dendritic cells and T-cells (Oda T et al). The fact that the $H_4$ receptor is highly distributed in cells of the immune system suggests the involvement of this receptor in immuno-inflammatory responses. Moreover, this hypothesis is reinforced by the fact that its gene expression can be regulated by inflammatory stimuli such as interferon, TNFα and IL-6. Nevertheless, the $H_4$ receptor is also expressed in other types of cells such as human synovial cells obtained from patients suffering from rheumatoid arthritis (Wojtecka-Lukasik E et al, *Ann Rheum Dis* 2006, 65 (Suppl 11): 129; Ikawa Y et al, *Bio/Pharm Bull* 2005, 28: 2016-8) and osteoarthritis (Grzybowska-Kowalczyk A of al, European Histamine Research Society XXXVI Annual Meeting, Florence, Italy, 2007, P-11), and in the human intestinal tract (Sander L E et al, *Gut* 2006, 55: 498-504). An increase in the expression of the $H_4$ receptor has also been reported in nasal polyp tissue in comparison to nasal mucosa of healthy people (Jókúti A et al, Cell Biol Int 2007, 31: 1367-70).

Recent studies with specific ligands of the $H_4$ receptor have helped to delimit the pharmacological properties of this receptor. These studies have evidenced that several histamine-induced responses in eosinophils such as chemotaxis, conformational change and CD11b and CD54 up-regulation are specifically mediated by the $H_4$ receptor (Ling P et al, *Br J Pharmacol* 2004, 142:161-71; Buckland K F et al, *Br J Pharmacol* 2003, 140:1117-27). In dendritic cells, the $H_4$ receptor has been shown to affect maturation, cytokine production and migration of these cells (Jelinek I et al, 1st Joint Meeting of European National Societies of Immunology, Paris, France, 2006, PA-1255). Moreover, the role of the $H_4$ receptor in mast cells has been studied. Although $H_4$ receptor activation does not induce mast cell degranulation, histamine and other proinflammatory mediators are released; moreover, the $H_4$ receptor has been shown to mediate chemotaxis and calcium mobilization of mast cells (Hofstra C L et al, *J Pharmacol Exp Ther* 2003, 305: 1212-21). With regard to T-lymphocytes; it has been shown that $H_4$ receptor activation induces T-cell migration and preferentially attracts a T-lymphocyte population with suppressor/regulatory phenotype and function (Morgan R K et al, *American Thoracic Society Conference*, San Diego, USA, 2006, P-536), as well as regulating the activation of CD4+ T cells (Dunford P J of al, *J Immunol* 2006, 176: 7062-70). As for the intestine, the distribution of the $H_4$ receptor suggests that it may have a role in the control of peristalsis and gastric acid secretion (Morini G of al, European Histamine Research Society XXXVI Annual Meeting, Florence, Italy, 2007, O-10).

The various functions of the $H_4$ receptor observed in eosinophils, mast cells and T-cells suggest that this receptor can play an Important role in the immuno-inflammatory response (see e.g. Zampeli E and Tiligada E, *Br J Pharmacol,* 2009, 157, 24-33). In fact, $H_4$ receptor antagonists have shown in vivo activity in murine models of peritonitis (Thurmond R L at al, *J Pharmacol Exp Ther* 2004, 309: 404-13), pleurisy (Takeshita K et al., *J Pharmacol Exp Ther* 2003, 307: 1072-8) and scratching (Bell J K et al, *Br J Pharmacol* 2004, 142:374-80). In addition, $H_4$ receptor antagonists have demonstrated in vivo activity in experimental models of allergic asthma (Dunford P J et al, 2006), inflammatory bowel disease (Varga C et al, *Eur J Pharmacol* 2005, 522:130-8), pruritus (Dunford P J at al, *J Allergy Clin Immunol* 2007, 119: 176-83), atopic dermatitis (Cowden J M at al, *J Allergy Clin Immunol* 2007; 119 (1): S239 (Abs 935), American Academy of Allergy, Asthma and Immunology 2007 AAAAI Annual Meeting, San Diego, USA), ocular inflammation (Zampeli E at at, European Histamine Research Society XXXVI Annual Meeting, Florence, Italy, 2007, O-36), edema and hyperalgesia (Coruzzi G of al, *Eur J Pharmacol* 2007, 563: 240-4), and neuropathic pain (Cowart M D at at, J Med. Chem. 2008; 51 (20): 6547-57). Histamine $H_4$ receptor antagonists may also be useful in cancer (see e.g. Cianchi F et al, *Clinical Cancer Research,* 2005, 11(19), 6807-6815).

It is therefore expected that $H_4$ receptor antagonists can be useful among others for the treatment or prevention of allergic, immunological and inflammatory diseases, pain and cancer.

Accordingly, it would be desirable to provide novel compounds having $H_4$ receptor antagonist activity and which are good drug candidates. In particular, preferred compounds should bind potently to the histamine $H_4$ receptor whilst showing little affinity for other receptors and ion channels. In addition to binding to $H_4$ receptors, compounds should further exhibit good pharmacological activity in in vivo disease models. Moreover, compounds should reach the target tissue or organ when administered via the chosen route of administration and possess favourable pharmacokinetic properties. In addition, they should be non-toxic and demonstrate few side-effects.

DESCRIPTION OF THE INVENTION

One aspect of the present invention relates to the compounds of formula I

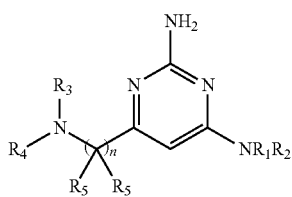

wherein:
$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more $C_{1-4}$alkyl groups; and
(ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;
wherein said heterocyclic groups (i) and (ii) are 4- to 7-membered monocyclic, 7- to 8-membered bridged bicyclic or 8- to 12-membered fused bicyclic;
or $R_1$ represents H or $C_{1-4}$alkyl, and $R_2$ represents azetidinyl, pyrrolidinyl, piperidinyl or azepanyl, which are optionally substituted with one or more $C_{1-4}$alkyl groups;
$R_a$ represents H or $C_{1-4}$alkyl;
$R_b$ represents H or $C_{1-4}$alkyl;
or $R_a$ and $R_b$ form, together with the N atom to which they are bound, an azetidinyl, pyrrolidinyl, piperidinyl or azepanyl group that is optionally substituted with one or more $C_{1-4}$alkyl groups;
$R_3$ represents H or $C_{1-8}$alkyl;
$R_4$ represents $C_{1-8}$alkyl optionally substituted with one or more halogen, $C_{3-10}$cycloalkyl-$C_{0-4}$alkyl, heterocycloalkyl-$C_{0-4}$alkyl, aryl-$C_{0-4}$alkyl or heteroaryl-$C_{0-4}$alkyl, wherein in the $C_{3-10}$cycloalkyl-$C_{0-4}$alkyl, heterocycloalkyl-$C_{0-4}$alkyl, aryl-$C_{0-4}$alkyl and heteroaryl-$C_{0-4}$alkyl groups any alkyl group is optionally substituted with one or more $R_6$ groups, any of the cycloalkyl and heterocycloalkyl groups are optionally substituted with one or more substituents independently selected from $C_{1-8}$alkyl and halogen, and any of the aryl and heteroaryl groups are optionally substituted with one or more $R_7$ groups;
each $R_5$ independently represents H or $C_{1-8}$alkyl;
each $R_6$ independently represents $C_{1-8}$alkyl, halogen, hydroxy$C_{0-6}$alkyl, $C_{3-10}$cycloalkyl optionally substituted with one or more $C_{1-8}$alkyl groups, or phenyl optionally substituted with one or more $R_8$; and optionally two $R_6$ groups on the same carbon atom are bonded together to form a —$C_{2-5}$alkylene- group which is optionally substituted with one or more $C_{1-8}$alkyl groups;
each $R_7$ independently represents $C_{1-8}$alkyl, halo$C_{1-6}$alkyl, halogen, $C_{1-6}$alkoxy, halo$C_{1-6}$alkoxy, —CN, $C_{1-6}$alkylthio, $C_{2-4}$alkynyl, hydroxy$C_{0-6}$alkyl, $CO_2R_9$—$C_{0-6}$alkyl, —$CONR_9R_9$, —$SO_2NR_9R_9$, —$SO_2$—$C_{1-6}$alkyl, —$NR_9SO_2$—$C_{1-6}$alkyl, —$NR_9CONR_9R_9$, —$NR_9COR_9$, —$NR_9R_9$, $C_{3-10}$cycloalkyl, heterocycloalkyl, aryl or heteroaryl; wherein any of the $C_{3-10}$ cycloalkyl, heterocycloalkyl, aryl or heteroaryl groups in $R_7$ are optionally substituted with one or more $C_{1-8}$ alkyl groups;
each $R_8$ independently represents $C_{1-8}$alkyl, halo$C_{1-6}$alkyl, halogen, $C_{1-6}$alkoxy, halo$C_{1-6}$alkoxy or —CN;
each $R_9$ independently represents H or $C_{1-8}$alkyl; and optionally two $R_9$ groups are bonded together to form a —$C_{3-5}$alkylene- group which is optionally substituted with one or more $C_{1-8}$alkyl groups; and
n represents 1 or 2.

The compounds of formula I show high affinity tot the $H_4$ histamine receptor and thus can be useful for the treatment or prevention of any disease mediated by this receptor.

Thus, another aspect of the invention relates to a compound of formula I

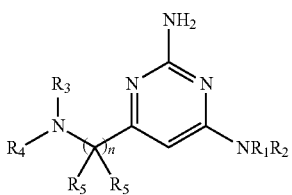

wherein:
$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more $C_{1-4}$alkyl groups; and
(i) a heterocyclic group which contains 1 N atom and does not contain any other heteroatom, wherein said heterocyclic group is substituted with one —$NR_aR_b$ group and is optionally substituted with one or more $C_{1-4}$alkyl groups;
wherein said heterocyclic groups (i) and (ii) are 4- to 7-membered monocyclic, 7- to 8-membered bridged bicyclic or 8- to 12-membered fused bicyclic;
or $R_1$ represents H or $C_{1-4}$alkyl, and $R_2$ represents azetidinyl, pyrrolidinyl, piperidinyl or azepanyl, which are optionally substituted with one or more $C_{1-4}$alkyl groups;
$R_a$ represents H or $C_{1-4}$alkyl;
$R_b$ represents H or $C_{1-4}$alkyl;
or $R_a$ and $R_b$ form, together with the N atom to which they are bound, an azetidinyl, pyrrolidinyl, piperidinyl or azepanyl group that is optionally substituted with one or more $C_{1-4}$alkyl groups;
$R_3$ represents H or $C_{1-6}$alkyl;
$R_4$ represents $C_{1-8}$alkyl optionally substituted with one or more halogen, $C_{3-10}$cycloalkyl-$C_{0-4}$alkyl, heterocycloalkyl-$C_{0-4}$alkyl, aryl-$C_{0-4}$alkyl or heteroaryl-$C_{0-4}$alkyl, wherein in the $C_{3-10}$cycloalkyl-$C_{0-4}$alkyl, heterocycloalkyl-$C_{0-4}$alkyl, aryl-$C_{0-4}$alkyl and heteroaryl-$C_{0-4}$alkyl groups any alkyl group is optionally substituted with one or more $R_6$ groups, any of the cycloalkyl and heterocycloalkyl groups are optionally substituted with one or more substituents independently selected from $C_{1-8}$alkyl and halogen, and any of the aryl and heteroaryl groups are optionally substituted with one or more $R_7$ groups;
each $R_5$ independently represents H or $C_{1-8}$alkyl;
each $R_6$ independently represents $C_{1-8}$alkyl, halogen, hydroxy$C_{0-6}$alkyl, $C_{3-10}$cycloalkyl optionally substituted with one or more $C_{1-8}$alkyl groups, or phenyl optionally substituted with one or more $R_8$; and optionally two $R_6$ groups on the same carbon atom are bonded together to form a —$C_{2-5}$alkylene- group which is optionally substituted with one or more $C_{1-8}$alkyl groups;

each $R_7$ independently represents $C_{1-8}$alkyl, halo$C_{1-5}$alkyl, halogen, $C_{1-6}$alkoxy, halo$C_{1-6}$alkoxy, —CN, $C_{1-6}$alkylthio, $C_{2-4}$alkynyl, hydroxy$C_{0-6}$alkyl, $CO_2R_9$—$C_{0-6}$alkyl, —$CONR_9R_9$, —$SO_2NR_9R_9$, —$SO_2$—$C_{1-6}$alkyl, —$NR_9SO_2$—$C_{1-6}$alkyl, —$NR_9CONR_9R_9$, —$NR_9COR_9$, —$NR_9R_9$, $C_{3-10}$cycloalkyl, heterocycloalkyl, aryl or heteroaryl; wherein any of the cycloalkyl, heterocycloalkyl, aryl or heteroaryl groups in $R_7$ are optionally substituted with one or more $C_{1-8}$alkyl groups;

each $R_8$ independently represents $C_{1-8}$alkyl, halo$C_{1-6}$alkyl, halogen, $C_{1-6}$alkoxy, halo$C_{1-6}$alkoxy or —CN;

each $R_9$ independently represents H or $C_{1-8}$alkyl; and optionally two $R_9$ groups are bonded together to form a —$C_{3-5}$alkylene- group which is optionally substituted with one or more $C_{1-8}$alkyl groups; and n represents 1 or 2;

for use in therapy.

Another aspect of the invention relates to a pharmaceutical composition Which comprises a compound of formula I or a pharmaceutically acceptable salt thereof and one or more pharmaceutically acceptable excipients.

Another aspect of the present invention relates to the use of a compound of formula I or a pharmaceutically acceptable salt thereof for the manufacture of a medicament for the treatment or prevention of a disease mediated by the histamine $H_4$ receptor. More preferably, the disease mediated by the histamine $H_4$ receptor is an allergic, immunological or inflammatory disease, pain or cancer.

Another aspect of the present invention relates to the use of a compound of formula I or a pharmaceutically acceptable salt thereof for the manufacture of a medicament for the treatment or prevention of an allergic, immunological or inflammatory disease, pain or cancer.

Another aspect of the present invention relates to the use of a compound of formula I or a pharmaceutically acceptable salt thereof for the manufacture of a medicament for the treatment or prevention of an allergic, immunological or inflammatory disease. More preferably, the allergic, immunological or inflammatory disease is selected from respiratory diseases, ocular diseases, skin diseases, inflammatory bowel diseases, autoimmune diseases, and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, eczema, dermatitis (e.g. atopic dermatitis), psoriasis, urticaria, pemphigus, dermatitis herpetiformis, cutaneous vasculitis, pruritus, ulcerative colitis, Crohn's disease, rheumatoid arthritis, multiple sclerosis, cutaneous lupus, systemic lupus erythematosus, systemic vasculitis and transplant rejection.

Another aspect of the present invention relates to the use of a compound of formula I or a pharmaceutically acceptable salt thereof for the manufacture of a medicament for the treatment or prevention of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a compound of formula I or a pharmaceutically acceptable salt thereof for use in the treatment or prevention of a disease mediated by the histamine $H_4$ receptor. More preferably, the disease mediated by the histamine $H_4$ receptor is an allergic, immunological or inflammatory disease, pain or cancer.

Another aspect of the present invention relates to a compound of formula I or a pharmaceutically acceptable salt thereof for use in the treatment or prevention of an allergic, immunological or inflammatory disease, pain or cancer.

Another aspect of the present invention relates to a compound of formula I or a pharmaceutically acceptable salt thereof for use in the treatment or prevention of an allergic, immunological or inflammatory disease. More preferably, the allergic, immunological or inflammatory disease is selected from respiratory diseases, ocular diseases, skin diseases, inflammatory bowel diseases, autoimmune diseases, and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, eczema, dermatitis (e.g. atopic dermatitis), psoriasis, urticaria, pemphigus, dermatitis herpetiformis, cutaneous vasculitis, pruritus, ulcerative colitis, Crohn's disease, rheumatoid arthritis, multiple sclerosis, cutaneous lupus, systemic lupus erythematosus, systemic vasculitis and transplant rejection.

Another aspect of the present invention relates to a compound of formula I or a pharmaceutically acceptable salt thereof for use in the treatment or prevention of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to the use of a compound of formula I or a pharmaceutically acceptable salt thereof for the treatment or prevention of a disease mediated by the histamine $H_4$ receptor. More preferably, the disease mediated by the histamine $H_4$ receptor is an allergic, immunological or inflammatory disease, pain or cancer.

Another aspect of the present invention relates to the use of a compound of formula I or a pharmaceutically acceptable salt thereof for the treatment or prevention of an allergic, immunological or inflammatory disease, pain or cancer.

Another aspect of the present invention relates to the use of a compound of formulator a pharmaceutically acceptable salt thereof for the treatment or prevention of an allergic, immunological or inflammatory disease. More preferably, the allergic, immunological or inflammatory disease is selected from respiratory diseases, ocular diseases, skin diseases, inflammatory bowel diseases, autoimmune diseases, and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, eczema, dermatitis (e.g. atopic dermatitis), psoriasis, urticaria, pemphigus, dermatitis herpetiformis, cutaneous vasculitis, pruritus, ulcerative colitis, Crohn's disease, rheumatoid arthritis, multiple sclerosis, cutaneous lupus, systemic lupus erythematosus, systemic vasculitis and transplant rejection.

Another aspect of the present invention relates to the use of a compound of formula I or a pharmaceutically acceptable salt thereof for the treatment or prevention of pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a method of treating or preventing a disease mediated by the histamine $H_4$ receptor in a subject in need thereof, preferably a human being, which comprises administering to said subject an amount of compound of formula I or a pharmaceutically acceptable salt thereof effective to treat or prevent said disease. More preferably, the disease mediated by the histamine H₄ receptor is an allergic, immunological or inflammatory disease, pain or cancer.

Another aspect of the present invention relates to a method of treating or preventing an allergic, immunological or inflammatory disease, pain or cancer in a subject in need thereof, preferably a human being, which comprises administering to said subject an amount of a compound of formula I or a pharmaceutically acceptable salt thereof effective to treat or prevent said allergic, immunological or inflammatory disease, pain or cancer.

Another aspect of the present invention relates to a method of treating or preventing an allergic, immunological or inflammatory disease in a subject in need thereof, preferably a human being, which comprises administering to said subject an amount of a compound of formula I or a pharmaceutically acceptable salt thereof effective to treat or prevent said disease. More preferably, the allergic, immunological or inflammatory disease is selected from respiratory diseases, ocular diseases, skin diseases, inflammatory bowel diseases, autoimmune diseases, and transplant rejection. Still more preferably, the allergic, immunological or inflammatory disease is selected from asthma, allergic rhinitis, chronic obstructive pulmonary disease (COPD), allergic rhinoconjunctivitis, dry eye, cataracts, eczema, dermatitis (e.g. atopic dermatitis), psoriasis, urticaria, pemphigus, dermatitis herpetiformis, cutaneous vasculitis, pruritus, ulcerative colitis, Crohn's disease, rheumatoid arthritis, multiple sclerosis, cutaneous lupus, systemic lupus erythematosus, systemic vasculitis and transplant rejection.

Another aspect of the present invention relates to a method of treating or preventing pain in a subject in need thereof, preferably a human being, which comprises administering to said subject an amount of a compound of formula I or a pharmaceutically acceptable salt thereof effective to treat or prevent said pain. More preferably, the pain is selected from inflammatory pain, inflammatory hyperalgesia, hyperalgesia, post-surgical pain, migraine, cancer pain, visceral pain, osteoarthritis pain and neuropathic pain.

Another aspect of the present invention relates to a process for the preparation of a compound of formula I as defined above, comprising:

(a) When in a compound of formula I n is 1, reacting a compound of formula II with a compound of formula III (or an amino-protected form thereof) in the presence of a reducing agent

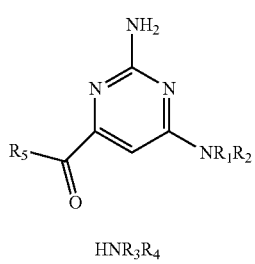

wherein $R_1$, $R_2$, $R_3$, $R_4$ and $R_5$ have the meaning described above, followed if necessary by the removal of any protecting group that may be present; or (b) When in a compound of formula I n is 1 and $R_5$ represents hydrogen, reacting a compound of formula IV with a compound of formula V (or an amino-protected form thereof)

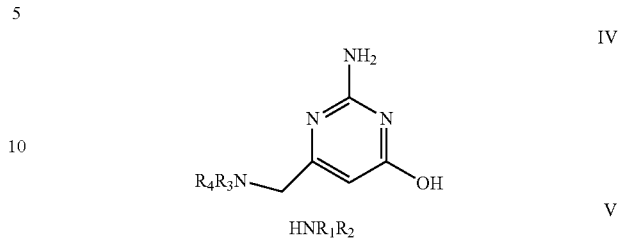

wherein $R_1$, $R_2$, $R_3$ and $R_5$ have the meaning described above, followed if necessary by the removal of any protecting group that may be present; or (c) When in a compound of formula I n is 1 and $R_5$ represents hydrogen, reacting a compound of formula IVb with a compound of formula V (or an amino-protected form thereof)

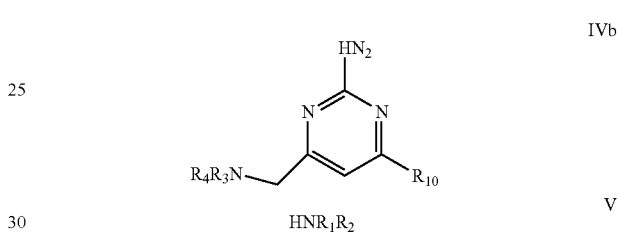

wherein $R_{10}$ represents a leaving group and $R_1$, $R_2$, $R_3$ and $R_4$ have the meaning described above, followed if necessary by the removal of any protecting group that may be present; or (d) When in a compound of formula I n is 1, reacting a compound of formula XX with a compound of formula III (or an amino-protected from thereof)

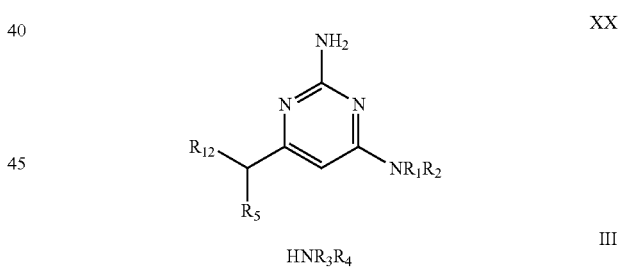

wherein $R_{12}$ represents a leaving group and $R_1$, $R_2$, $R_3$ $R_4$ and $R_5$ have the meaning described above, followed if necessary by the removal of any protecting group that may be present; or (e) When in a compound of formula I n=1 and $R_5$ represents H or n=2 and $(CR_5R_5)_2$ represents —(CH₂)—(CR₅R₅)—, treating a compound of formula XIV with a reducing agent

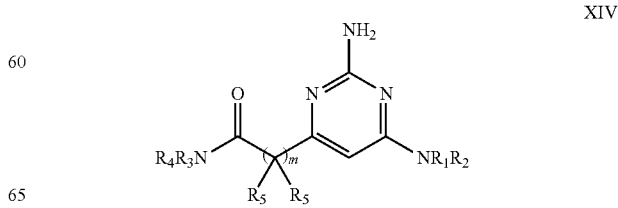

wherein $R_1$, $R_2$, $R_3$ $R_4$ and $R_5$ have the meaning described above and m is 0 or 1; or (f) transforming a compound of formula I into another compound of formula I in one or in several steps.

In the previous definitions, the term $C_{1-y}$alkyl refers to a linear or branched alkyl chain containing from 1 to y carbon atoms. For example, a $C_{1-4}$alkyl group refers to a linear or branched alkyl chain containing from 1 to 4 C atoms and includes methyl, ethyl, propyl, isopropyl, butyl, isobutyl, sec-butyl and tert-butyl. The term $C_0$alkyl indicates that the alkyl group is absent.

A halo$C_{1-6}$alkyl group means a group resulting from the substitution of one or more hydrogen atoms of a $C_{1-6}$ alkyl group with one or more halogen atoms (i.e. fluoro, chloro, bromo or iodo) that can be the same or different. Examples include, amongst others, trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, nonafluorobutyl, 5,5,5-trifluoropentyl and 6,6,6-trifluorohexyl.

Likewise, the term $C_{1-8}$alkyl optionally substituted with one or more halogen means a group resulting from the substitution of one or more hydrogen atoms of a $C_{1-8}$alkyl group with one or more halogen atoms (i.e. fluoro, chloro, bromo or iodo) that can be the same or different. Preferably the halogen atom(s) is/are fluoro.

A $C_{1-6}$alkoxy group relates to a group of formula $C_{1-6}$alkyl-O—, wherein the alkyl moiety has the same meaning as defined above. Examples include, amongst others, methoxy, ethoxy, propoxy, isopropoxy, butoxy, isobutoxy, sec-butoxy, tert-butoxy, pentyloxy and hexyloxy.

A halo$C_{1-6}$alkoxy group means a group resulting from the substitution of one or more hydrogen atoms of a $C_{1-6}$alkoxy group with one or more halogen atoms (i.e. fluoro, chloro, bromo or iodo) that can be the same or different. Examples include, amongst others, trifluoromethoxy, fluoromethoxy, 1-chloroethoxy, 2-chloroethoxy, 1-fluoroethoxy, 2-fluoroethoxy, 2-bromoethoxy, 2-iodoethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy, nonafluorobutoxy, 2-chtoropentyloxy and 3-chlorohexyloxy.

A $C_{1-6}$alkylthio group means a group of formula $C_{1-6}$alkyl-S—, wherein the alkyl residue has the same meaning as that previously defined. Examples include methylthio, ethylthio, propylthio, isopropylthio, butylthio, isobutylthio, sec-butylthio, tert-butylthio, pentylthio and hexylthio.

A $C_{2-4}$alkynyl group means a linear or branched alkyl chain which contains from 2 to 4 carbon atoms and which further contains one or two triple bonds. Examples include, among others, the ethynyl, 1-propynyl, 2-propynyl, 1-butynyl, 2-butynyl, 3-butynyl and 1,3-butadiynyl groups.

The term hydroxy$C_{0-6}$alkyl includes hydroxy and hydroxy$C_{1-6}$alkyl.

A hydroxy$C_{1-6}$alkyl group means a group resulting from the replacement of one or more hydrogen atoms of a $C_{1-6}$alkyl group with one or more hydroxy groups. Preferably, the $C_{1-6}$alkyl group is substituted with one hydroxy group. Examples include, among others, the groups hydroxymethyl, 1-hydroxyethyl, 2-hydroxyethyl, 1,2-dihydroxyethyl, 3-hydroxypropyl, 2-hydroxypropyl, 1-hydroxypropyl, 2,3-dihydroxypropyl, 4-hydroxybutyl, 3-hydroxybutyl, 2-hydroxybutyl, 1-hydroxybutyl, 5-hydroxypentyl and 6-hydroxyhexyl.

The term $CO_2R_9$—$C_{0-9}$alkyl includes —$CO_2R_9$ and $CO_2R_9$—$C_{1-6}$alkyl.

A $CO_2R_9$—$C_{1-6}$alkyl group means a group resulting from the replacement of one or more hydrogen atoms of a $C_{1-6}$alkyl group with one or more —$CO_2R_9$ groups. Preferably, the $C_{1-6}$alkyl group is substituted with one —$CO_2R_9$ group.

A —$C_{x-5}$alkylene- group, in relation to the group formed either by two $R_6$ groups on the same carbon atom or by two $R_9$ groups (which can be either on the same atom as e.g. in —$CONR_9R_9$ or on different atoms as e.g. in —$NR_9COR_9$ or —$NR_9CONR_9R_9$), refers to a linear alkyl chain which contains from x to 5 carbon atoms, i.e. a group of formula —$(CH_2)_{x-5}$—. As indicated in the definition of a compound of formula I, the —$C_{x-5}$alkylene- group is optionally substituted with one or more $C_{1-8}$alkyl groups, preferably with one or more methyl groups. Examples of two $R_6$ on the same carbon atom forming together a —$C_{2-5}$alkylene- group include, among others:

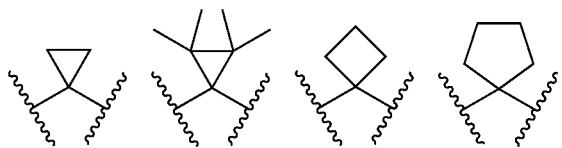

Examples of two $R_9$ groups which together form a —$C_{3-5}$ alkylene- group include, among others:

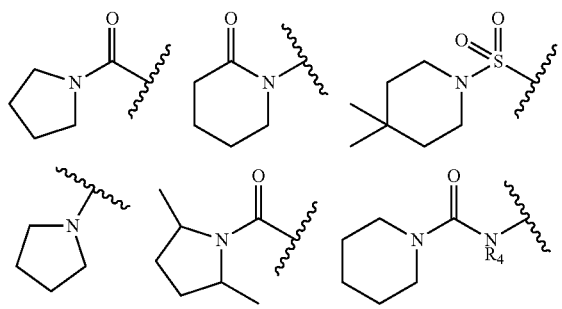

A $C_{3-10}$cycloalkyl group, either as a group or as part of a $C_{3-10}$cycloalkyl-$C_{0-4}$alkyl group, relates to a saturated carbocyclic ring having from 3 to 10 carbon atoms that is monocyclic or polycyclic. One or two C atoms of the carbocyclic ring may optionally be oxidized forming CO groups. The cycloalkyl group may be bound through any available C atom. Examples include, amongst others, cyclopropyl, cyclobutyl, cyclopentyl, cyclohexyl, cycloheptyl, cyclooctyl, cyclopentanonyl, bicyclo[3.1.1]heptan-3-yl, bicyclo[2.2.1]heptanyl, bicyclo[2.2.2]octanyl or adamantyl.

The term $C_{3-10}$cycloalkyl-$C_{1-4}$alkyl includes $C_{3-10}$cycloalkyl and $C_{3-10}$cycloalkyl-$C_{1-4}$alkyl.

A $C_{3-10}$cycloalkyl-$C_{1-4}$alkyl group means a group resulting from the substitution of one or more hydrogen atoms of a $C_{1-4}$alkyl group with one or more cycloalkyl groups, which may be the same or different. Preferably, the $C_{1-4}$alkyl group is substituted with one or two cycloalkyl groups, and more preferably it is substituted with one cycloalkyl group. The cycloalkyl group may substitute either one H atom on a C atom or two H atoms on the same C atom of the alkyl group (in which case the cycloalkyl group shares one C atom with the alkyl group), such as in the groups shown as examples below:

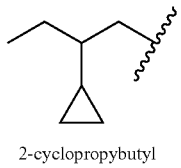
2-cyclopropybutyl

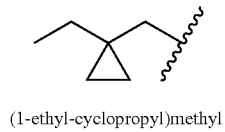
(1-ethyl-cyclopropyl)methyl butyl group where 1H atom on a C atom butyl group where 2H atoms on a same C atom is substituted with a cyclopropyl group are substituted with a cyclopropyl group Examples of $C_{3-10}$cycloalkyl-$C_{1-4}$alkyl groups include, amongst others, cyclopropylmethyl, cyclobutylmethyl, cyclopentylmethyl, cyclohexylmethyl, cycloheptylmethyl, cyclooctylmethyl, bicyclo[2.2.1]heptanylmethyl, dicyclopropylmethyl, (1-methyl-cyclopropyl)methyl, (1-ethyl-cyclopropyl)methyl, (1-cyclopentylmethyl-cyclopropyl)methyl, 2-cyclopropylethyl, 2-cyclobutylethyl, 2-cyclopentylethyl, 2-cyclohexylethyl, 2,2-dicyclopropylethyl, 2-cyclohexyl-2-cyclopropyl-ethyl, 2-(1-methyl-cyclopropyl)ethyl, 1-cyclopropyl-1-methylethyl, 1-cyclopropylethyl, 1-cyclobutylethyl, 1-cyclopentylethyl, 1-cyclohexylethyl, 3-cyclopropylpropyl, 3-cyclobutylpropyl, 3-cyclopentylpropyl, 3-cyclohexylpropyl, 1-cyclopropyl-2-methylpropyl, 4-cyclopropylbutyl, 3-cyclopropylbutyl, 2-cyclopropylbutyl, 1-cyclopropylbutyl, 4-cyclobutylbutyl, 4-cyclopentylbutyl and 4-cyclohexylbutyl.

A heterocycloalkyl group, either as a group or as part of a heterocycloalkyl-$C_{0-4}$alkyl group, relates to a saturated heterocyclic ring having from 3 to 10 carbon atoms and up to three heteroatoms independently selected from N, O and S that can be a monocyclic or polycyclic. From one to three C, N or S atoms of the heterocyclic ring may optionally be oxidized forming CO, NO, SO or $SO_2$ groups, respectively. The heterocycloalkyl group may be bound through any available C or N atom. Examples of heterocycloalkyl groups include, among others, oxiranyl, azetidinyl, oxetanyl, tetrahydrofuranyl, pyrrolidinyl, pyrazolidinyl, isothiazolidinyl, piperidinyl, morpholinyl, piperazinyl, 2-oxo-tetrahydrofuranyl, 2-oxo-[1,3]dioxolanyl, 2-oxo-oxazolidinyl, 2-oxo-imidazolidinyl, 2-oxo-[1,3]oxazinanyl, 2-oxo-piperazinyl, thiomorpholinyl, 1,1-dioxo-thiomorpholinyl, azepanyl, [1,4]diazepanyl, [1,4]oxazepanyl, 2-oxo-azepanyl, 1,1-dioxo-(1,2)thiazepanyl, 2-oxo-[1,3]diazepanyl, 7-oxo-bicyclo[2.2.1]heptanyl and 1,3-diaza-bicyclo[2.2.2]octanyl.

The term heterocycloalkyl-$C_{0-4}$alkyl includes heterocycloalkyl and heterocycloalkyl-$C_{1-4}$alkyl.

A heterocycloalkyl-$C_{1-4}$alkyl group relates to a group resulting from the substitution of one or more hydrogen atoms of a $C_{1-4}$alkyl group with one or more heterocycloalkyl groups which may be the same or different. Preferably, the $C_{1-4}$alkyl group is substituted with one or two heterocycloalkyl groups, and more preferably, is substituted with one heterocycloalkyl group. Examples of heterocycloalkyl-$C_{1-4}$alkyl groups include, among others, pyrrolidin-2-ylmethyl, pyrrolidin-3-ylmethyl, morpholin-3-ylmethyl, tetrahydrofuran-2-ylmethyl, (2-oxo-(1,3)oxazinan-6-yl)-methyl, 2-piperidin-3-yl-ethyl, 2-piperazin-1-yl-propyl, 1-methyl-2-piperazin-1-yl-ethyl, 2-methyl-3-(pyrrolidin-3-yl)-propyl, 3-methyl-4-piperazin-1-yl-butyl and 4-(tetrahydrofuran-3-yl)-butyl.

The term aryl, either as a group or as part of an aryl-$C_{0-4}$alkyl group, relates to phenyl or naphthyl. Preferably, aryl represents phenyl. The term aryl also includes fused benzocycloalkyl groups, such as dihydroindenyl and tetrahydronaphthalenyl. The fused benzo-cycloalkyl group may be bound through any available C atom of either the saturated or the aromatic fragment.

The term aryl-$C_{0-4}$alkyl includes aryl and aryl-$C_{1-4}$alkyl.

An aryl-$C_{1-4}$alkyl group means a group resulting from the substitution of one or more hydrogen atoms of a $C_{1-4}$alkyl group with one or more aryl groups, preferably with one or two aryl groups and more preferably with one aryl group, which can be the same or different. Examples of aryl-$C_{1-4}$ alkyl include, amongst others, the groups benzyl, 1-phenylethyl, 2-phenylethyl, 1-phenyl-1-methylethyl, 2,2-diphenylethyl, 3-phenylpropyl, 2-phenyl-1-methylpropyl and 4-phenylbutyl.

The term heteroaryl, either as a group or as part of a heteroaryl-$C_{0-4}$alkyl group, relates to a monocyclic aromatic ring of 5 or 6 members or bicyclic aromatic ring of 8 to 12 members which contains up to four heteroatoms independently selected from nitrogen, oxygen and sulphur. The heteroaryl group may be bound to the residue of the molecule through any available C or N atom. Examples of heteroaryl groups include among others 1,2,4-oxadiazolyl, 1,2,4-thiadiazolyl, 1,3,4-oxadiazolyl, 1,3,4-thiadiazolyl, furanyl, imidazolyl, isoxazolyl, isothiazolyl, oxazolyl, pyrazolyl, pirrolyl, thiazolyl, thiophenyl, 1,2,3-triazolyl, 1,2,4-triazolyl, pyrazinyl, pyridazinyl, pyridinyl, pyrimidinyl, benzimidazolyl, benzofuranyl, benzothiazolyl, benzothiophenyl, imidazopyrazinyl, imidazopyridazinyl, imidazopyridinyl, imidazopyrimidinyl, indazotyl, indolyl, isoindolyl, isoquinolinyl, naphthyridinyl, pyrazolopyrazinyl, pyrazolopyridinyl, pyrazolopyrimidinyl, purinyl, quinazolinyl, quinolinyl and quinoxalinyl. In the definition of heteroaryl when the examples specified refer to a bicycle in general terms, they include all possible arrangements of the atoms. For example, the term pyrazolopyridinyl includes groups such as 1H-pyrazolo[3,4-b]pyridinyl, pyrazolo[1,5-a]pyridinyl, 1H-pyrazolo[3,4-d]pyridinyl, 1H-pyrazolo[4,3-d]pyridinyl and 1H-pyrazolo[4,3-b]pyridinyl; the term imidazopyrazinyl includes groups such as 1H-imidazo[4,5-b]pyrazinyl, imidazo[1,2-a]pyrazinyl and imidazo[1,5-a]pyrazinyl and the term pyrazolopyrimidinyl includes groups such as 1H-pyrazolo[3,4-d]pyrimidinyl, 1H-pyrazolo[4,3-d]pyrimidinyl, pyrazolo[1,5-a]pyrimidinyl and pyrazolo[1,5-c]pyrimidinyl. The term heteroaryl also includes fused benzo-heterocycloalkyl groups, such as 2,3-dihydro-1H-indolyl and 2-oxo-2,3-dihydro-1H-indolyl. The fused benzo-heterocycloalkyl group may be bound through any available C or N atom of the saturated fragment or through any available C atom of the aromatic fragment.

The term heteroaryl-$C_{0-4}$alkyl includes heteroaryl and heteroaryl-$C_{1-4}$alkyl.

A heteroaryl-$C_{1-4}$alkyl group relates to a group resulting from the substitution of one of more hydrogen atoms of a $C_{1-4}$alkyl group with one or more heteroaryl groups which may be the same or different. Preferably, the $C_{1-4}$alkyl group is substituted with one or two heteroaryl groups and, more preferably, is substituted with one heteroaryl group. Examples of heteroaryl-$C_{1-4}$alkyl include, among others, 1H-pyrazol-3-yl-methyl, furan-2-yl-methyl, pyridine-3-yl-methyl, quinolin-3-ylmethyl, oxazol-2-ylmethyl, 1H-pyrrol-2-ylmethyl, 1-pyridine-3-yl-ethyl, 2-pyridine-2-yl-propyl, 3-pyridine-3-yl-propyl, 1-methyl-2-pyridine-3-yl-propyl, 4-pyridine-2-yl-butyl and 3-pyridine-2-yl-butyl.

In a compound of formula I, as indicated in the definition of $R_4$ regarding the terms $C_{3-10}$cycloalkyl-$C_{1-4}$alkyl, heterocycloalkyl-$C_{0-4}$alkyl, aryl-$C_{0-4}$alkyl or heteroaryl-$C_{0-4}$alkyl, any alkyl group is optionally substituted with one or more $R_6$ groups. This refers to the $C_{0-4}$alkyl group that forms part of the $C_{3-10}$cycloalkyl-$C_{0-4}$alkyl, heterocycloalkyl-$C_{0-4}$alkyl, aryl-$C_{0-4}$alkyl or heteroaryl-$C_{0-4}$alkyl groups. When $R_6$ represents $C_{1-8}$alkyl, halogen, hydroxy$C_{0-6}$alkyl, cycloalkyl optionally substituted with one or more $C_{1-8}$alkyl groups, or phenyl optionally substituted with one or more $R_8$ then preferably said $C_{0-4}$alkyl group is optionally substituted with one $R_6$ group.

As indicated in the definition of $R_4$ in a compound of formula I, any of the cycloalkyl and heterocycloalkyl groups are optionally substituted with one or more substituents independently selected from $C_{1-8}$alkyl and halogen, and any of the aryl and heteroaryl groups are optionally substituted with one or more $R_7$ groups. Preferably the cycloalkyl, heterocycloalkyl, aryl and heteroaryl groups are optionally substituted with one substituent.

A halogen group or its abbreviation halo means fluoro, chloro, bromo or iodo. Preferred halogen atoms are fluoro and chloro, and more preferably fluoro.

The term "saturated" relates to groups that do not have any double or triple bonds.

A "bridged bicyclic" group refers to a bicyclic system having two common atoms (bridgeheads) connecting three acyclic chains (bridges), so that the two bridges with the higher number of atoms form then the main ring and the bridge with the lower number of atoms is the "bridge".

A "fused bicyclic" group refers to a bicyclic system consisting of two adjacent rings sharing two atoms in common.

In the definition of $NR_1R_2$ $R_1$ and $R_2$ together with the N atom to which they are bound form a heterocyclic group of type (i) or (ii). A heterocyclic group of type (i) is a saturated heterocyclic group which contains 2 N atoms and does not contain any other heteroatom and which is 4- to 7-membered monocyclic, 7- to 8-membered bridged bicyclic or 8- to 12-membered fused bicyclic. Examples include, among others, piperazinyl, homopiperazinyl, 2.5-diaza-bicyclo[2.2.1]heptanyl, 2,5-diaza-bicyclo[2.2.2]octanyl, octahydro-pyrrolo[1,2-a]pyrazinyl, octahydro-pyrrolo[3,4-b]pyridinyl, octahydro-pyrrolo[3,2-c]pyridinyl and octahydropyrrolo[3,4-c]pyrrolinyl. Said groups are optionally substituted with one or more $C_{1-4}$alkyl groups, which can be the same or different and which are placed at any available C or N atom.

A heterocyclic group of type (ii) is a saturated heterocyclic group which contains 1 N atom and does not contain any other heteroatom, wherein said heterocyclic group is substituted with one —$NR_aR_b$ group, and which is 4- to 7-membered monocyclic, 7- to 8-membered bridged bicyclic or 8- to 12-membered fused bicyclic, preferably 4- to 7-membered monocyclic. Examples of (ii) include, among others, 3-amino-azetidinyl, 3-methylamino-azetidinyl, 3-dimethylamino-azetidinyl, 3-amino-pyrrolidinyl, 3-methylamino-pyrrolidinyl, 3-dimethylamino-pyrrolidinyl, 4-amino-piperidinyl, 4-methylamino-piperidinyl, 4-dimethylamino-piperidinyl and 6-methylamino-3-aza-bicyclo[3.1.0]hexane-3-yl. Said groups are further optionally substituted with one or more $C_{1-4}$alkyl groups, which can be the same or different, as indicated above in the definition of a compound of formula I.

In the definition of a compound of formula I n represents 1 or 2. The —$(CR_5R_5)_n$— group thus represents a group of formula —$CR_5R_5$— or —$CR_5R_5$—$CR_5R_5$—.

When in the definition of a substituent two or more groups with the same numbering are indicated (e.g. —$CR_5R_5$—, —$CONR_9R_9$, —$SO_2NR_9R_9$, or —$NR_9R_9$ etc.), this does not mean that they must be the same. Each of them is independently selected from the list of possible meanings given for said group, and therefore they can be the same or different.

The expression "optionally substituted with one or more" means that a group can be substituted with one or more, preferably 1, 2, 3 or 4, more preferably 1, 2 or 3, and more preferably 1 or 2 substituents, provided that said group has enough positions available susceptible of being substituted. These substituents are always independently selected from the list of possible meanings given for said substitutent and can thus be the same or different, and can be located at any available position.

Throughout the present specification, by the term 'treatment' is meant eliminating, reducing or ameliorating the cause or the effects of a disease. For purposes of this invention treatment includes, but is not limited to, alleviation, amelioration or elimination of one or more symptoms of the disease; diminishment of the extent of the disease; stabilized (i.e. not worsening) state of disease; delay or slowing of disease progression; amelioration or palliation of the disease state; and remission of the disease (whether partial or total).

As used herein, "prevention" refers to preventing the occurrence of a disease in a subject that is predisposed to or has risk factors but does not yet display symptoms of the disease. Prevention includes also preventing the recurrence of a disease in a subject that has previously suffered said disease.

Any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{16}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of the invention can generally be prepared by carrying out the procedures disclosed in the schemes or in the examples and preparations described below by substituting a readily available isotopically labeled reagent for a non-isotopically labeled reagent. In addition to the unlabeled form, all isotopically labeled forms of the compounds of formula I are included within the scope of the invention.

The invention therefore relates to the compounds of formula I as defined above.

In another embodiment, the invention relates to compounds of formula I wherein n is 1.

In another embodiment, the invention relates to compounds of formula I wherein $R_5$ is H.

In another embodiment, the invention relates to compounds of formula I wherein $R_3$ is H or methyl.

In another embodiment, the invention relates to compounds of formula I wherein $R_3$ is H.

In another embodiment, the invention relates to compounds of formula I wherein:

$R_1$ and $R_2$ form, together with the N atom to which they are bound, a saturated heterocyclic group selected from:

(i) a heterocyclic group which contains 2 N atoms and does not contain any other heteroatom, wherein said heterocyclic group is optionally substituted with one or more $C_{1-4}$alkyl groups; and (ii) a heterocyclic group which contains 1 N atom and does not contain any other heteroatom, wherein said heterocyclic group is substituted with one —$NR_aR_b$ group and is optionally substituted with one or more CIA alkyl groups;

wherein said heterocyclic groups (i) and (ii) are 4- to 7-membered monocyclic, 7- to 8-membered bridged bicyclic or 8- to 12-membered fused bicyclic.

In another embodiment, the invention relates to compounds of formula I wherein $R_a$ and $R_b$ independently represent H or $C_{1-4}$alkyl, preferably H, methyl or ethyl and more preferably H or methyl.

In another embodiment, the invention relates to the compounds of formula I wherein $R_a$ represents H and $R_b$ represents $C_{1-4}$alkyl, preferably H, methyl or ethyl and more preferably H or methyl.

In another embodiment, the invention relates to the compounds of formula I wherein $R_a$ represents H and $R_b$ represents $C_{1-4}$alkyl, preferably methyl or ethyl and more preferably methyl.

In another embodiment, the invention relates to compounds of formula I wherein $R_a$ and $R_b$ represent H.

In another embodiment, the invention relates to compounds of formula I wherein $R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and can be optionally substituted with one or more $C_{1-4}$alkyl groups; wherein said heterocyclic group is 4- to 7-membered monocyclic, 7- to 8-membered bridged bicyclic or 8- to 12-membered fused bicyclic.

In another embodiment, the invention relates to compounds of formula I wherein $R_1$ and $R_2$ form, together with the N atom to which they are bound, a saturated heterocyclic group selected from:

(a)
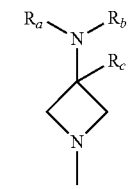

(b)
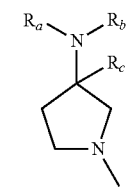

(c)
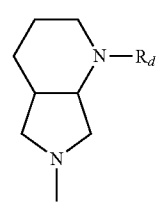

(d)
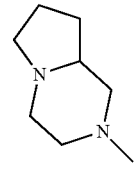

(e)
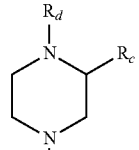

(f)
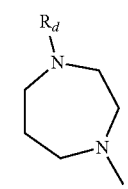

(g)
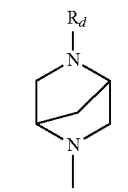

(h)
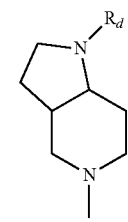

wherein $R_a$ and $R_b$ have the meaning described above for compounds of formula I, $R_c$ represents H or $C_{1-4}$alkyl, preferably H or methyl, more preferably H, and $R_d$ represents H or $C_{1-4}$alkyl, preferably H or methyl.

In another embodiment, the invention relates to compounds of formula I wherein $R_1$ and $R_2$ form, together with the N atom to which they are bound, a saturated heterocyclic group selected from (a) to (h), and $R_a$, $R_b$, $R_c$ and $R_d$ independently represent H or CIA alkyl, preferably $R_a$, $R_b$, $R_c$ and $R_d$ independently represent H or methyl, and more preferably $R_a$, $R_b$ and $R_d$ independently represent H or methyl and $R_c$ represents H.

In another embodiment, the invention relates to compounds of formula I wherein $R_1$ and $R_2$ form, together with the N atom to which they are bound, a saturated heterocyclic group selected from (a), (b) and (e), wherein $R_a$ and $R_b$ have the meaning described above for compounds of formula I, $R_c$ represents H or $C_{1-4}$alkyl and $R_d$ represents H or $C_{1-4}$alkyl; preferably $R_a$, $R_b$, $R_c$ and $R_d$ independently represent H or $C_{1-4}$alkyl, more preferably $R_a$, $R_b$, $R_c$ and $R_d$ independently represent H or methyl, and still more preferably $R_a$, $R_b$ and $R_d$ independently represent H or methyl and $R_c$ represents H, and even more preferably $R_a$ represents H, $R_b$ represents methyl, $R_c$ represents H and $R_d$ represents H or methyl.

In another embodiment, the invention relates to compounds of formula I wherein $R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or Cu alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H.

In another embodiment, the invention relates to the compounds of formula I wherein $R_1$ and $R_2$ form, together with the N atom to which they are bound, a saturated heterocyclic group of formula (a), wherein $R_a$ and $R_b$ have the meaning described above for compounds of formula I and $R_b$ represents H or $C_{1-4}$alkyl, preferably $R_a$, $R_b$ and $R_d$ independently represent H or Cu alkyl, more preferably $R_a$, $R_b$, and $R_c$ independently represent H or methyl, still more preferably $R_a$ and $R_b$ independently represent H or methyl and $R_d$ represents H, even more preferably $R_a$ represents H, $R_b$ represents H or methyl and $R_c$ represents H and particularly preferably $R_1$ represents H, $R_b$ represents methyl and $R_b$ represents H.

In another embodiment, the invention relates to the compounds of formula I wherein $R_1$ and $R_2$ form, together with the N atom to which they are bound, a saturated heterocyclic group of formula (b), wherein $R_a$ and $R_b$ have the meaning described above for compounds of formula I and $R_d$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_d$ represents H, even more preferably $R_a$ represents H, $R_b$ represents H or methyl and $R_c$ represents H and particularly preferably $R_a$ represents H, $R_b$ represents methyl and $R_c$ represents H.

In another embodiment, the invention relates to compounds of formula I wherein $R_1$ represents H or $C_{1-4}$ alkyl and $R_2$ represents azetidinyl, pyrrolidinyl, piperidinyl or azepanyl, which are optionally substituted with one or more $C_{1-4}$alkyl groups.

In another embodiment, the invention relates to compounds of formula I wherein $R_1$ represents H and $R_2$ represents 1-methyl-pyrrolidin-3-yl or pyrrolidin-3-yl.

In another embodiment, the invention relates to compounds of formula I wherein $R_4$ represents $C_{1-8}$alkyl, $C_{3-10}$cycloalkyl-$C_{0-4}$alkyl, heterocycloalkyl-$C_{0-4}$alkyl, aryl-$C_{0-4}$alkyl or heteroaryl-$C_{0-4}$alkyl, wherein in the $C_{3-10}$cycloalkyl-$C_{0-4}$alkyl, heterocycloalkyl-$C_{0-4}$alkyl, aryl-Cod alkyl and heteroaryl-$C_{0-4}$alkyl groups any alkyl group is optionally substituted with one or more $R_6$ groups, any of the cycloalkyl and heterocycloalkyl groups are optionally substituted with one or more substituents independently selected from $C_{1-8}$alkyl and halogen, and any of the aryl and heteroaryl groups are optionally substituted with one or more $R_7$ groups.

In another embodiment, the invention relates to compounds of formula I wherein $R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups.

In another embodiment, the invention relates to compounds of formula I wherein $R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein &represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$alkyl or aryl-$C_{0-2}$alkyl; wherein in the aryl-$C_{0-4}$alkyl and aryl-$C_{0-2}$alkyl groups any aryl is optionally substituted with one or more $R_7$ groups.

In another embodiment, the invention relates to compounds of formula I wherein $R_4$ represents $C_{1-8}$alkyl optionally substituted with one or more halogen, or $C_{3-10}$cycloalkyl-$C_{0-4}$alkyl, wherein in the $C_{3-10}$cycloalkyl-$C_{0-4}$alkyl group the alkyl group is optionally substituted with one or more $R_6$ groups and the cycloalkyl group is optionally substituted with one or more substituents independently selected from $C_{1-8}$alkyl and halogen.

In another embodiment, the invention relates to compounds of formula I wherein $R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$ alkyl and halogen.

In another embodiment, the invention relates to compounds of formula I wherein $R_4$ represents $C_{1-8}$alkyl or $C_{3-10}$cycloalkyl-$C_{0-4}$-alkyl, wherein in the $C_{3-10}$cycloalkyl-$C_{0-4}$alkyl group the cycloalkyl group is optionally substituted with one or more substituents independently selected from $C_{1-6}$alkyl and halogen.

In another embodiment, the invention relates to compounds of formula I wherein $R_4$ represents $C_{3-8}$alkyl optionally substituted with one or more halogen or $C_{3-6}$cycloalkyl-$C_{0-1}$alkyl, wherein in the $C_{3-6}$cycloalkyl-$C_{0-1}$alkyl group the cycloalkyl group is optionally substituted with one or more substituents independently selected from $C_{1-8}$ alkyl and halogen.

In another embodiment, the invention relates to compounds of formula I wherein $R_4$ represents $C_{3-8}$alkyl or $C_{3-6}$cycloalkyl-$C_{0-1}$alkyl, wherein in the $C_{3-6}$cycloalkyl-$C_{0-1}$ alkyl group the cycloalkyl group is optionally substituted with one or more substituents independently selected from $C_{1-8}$alkyl and halogen.

In another embodiment, the invention relates to compounds of formula I wherein $R_4$ represents $C_{1-8}$alkyl, preferably $C_{3-8}$alkyl.

In another embodiment, the invention relates to compounds of formula I wherein $R_4$ represents $C_{3-10}$ cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen.

In another embodiment, the invention relates to compounds of formula I wherein $R_4$ represents $C_{3-10}$ cycloalkyl-$C_{0-4}$alkyl, preferably $C_{3-10}$cycloalkyl-$C_{0-4}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein $R_4$ represents $C_{3-10}$ cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any cycloalkyl is optionally substituted with one or more substituents independently selected from $C_{1-8}$alkyl and halogen.

In another embodiment, the invention relates to compounds of formula I wherein $R_4$ represents $C_{3-10}$ cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl.

In another embodiment, the invention relates to compounds of formula I wherein $R_4$ represents $C_{3-10}$ cycloalkyl-$C_1$alkyl, preferably $C_{3-6}$cycloalkyl-$C_1$alkyl, wherein any alkyl is optionally substituted with one or more $R_6$ groups and any cycloalkyl is optionally substituted with one or more substituents independently selected from $C_{1-8}$ alkyl and halogen.

In another embodiment, the invention relates to compounds of formula I wherein $R_4$ represents $C_{3-10}$ cycloalkyl-$C_1$alkyl, preferably $C_{3-6}$cycloalkyl-$C_1$alkyl, wherein any alkyl is optionally substituted with one or more $R_6$ groups and any cycloalkyl is optionally substituted with one or more substituents independently selected from $C_{1-8}$ alkyl and halogen; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein $R_4$ represents $C_{3-10}$ cycloalkyl-$C_1$alkyl, preferably $C_{3-6}$cycloalkyl-$C_1$alkyl, more preferably cyclopropylmethyl.

In another embodiment, the invention relates to compounds of formula I wherein $R_4$ represents $C_{3-10}$ cycloalkyl, preferably $C_{3-6}$cycloalkyl and more preferably cyclopentyl, wherein any cycloalkyl is optionally substituted with one or more substituents independently selected from $C_{1-8}$alkyl and halogen.

In another embodiment, the invention relates to compounds of formula I wherein $R_4$ represents $C_{3-10}$ cycloalkyl, preferably $C_{3-6}$cycloalkyl and more preferably cyclopentyl.

In another embodiment, the invention relates to compounds of formula I wherein $R_4$ represents aryl-$C_{0-4}$ alkyl, preferably aryl-$C_{0-2}$alkyl and more preferably phenyl-$C_{0-2}$ alkyl, wherein any alkyl is optionally substituted with one or more $R_5$ groups and any aryl is optionally substituted with one or more $R_7$ groups.

In another embodiment, the invention relates to compounds of formula I wherein $R_4$ represents aryl-$C_{0-4}$ alkyl, preferably aryl-$C_{0-2}$alkyl and more preferably phenyl-$C_{0-2}$ alkyl, wherein any alkyl is optionally substituted with one or more $R_6$ groups and any aryl is optionally substituted with one or more $R_7$ groups; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein $R_4$ represents aryl-$C_{0-4}$ alkyl, preferably aryl-$C_{0-2}$alkyl and more preferably phenyl-$C_{0-2}$ alkyl.

In another embodiment, the invention relates to compounds of formula I wherein $R_4$ represents aryl-$C_{1-2}$ alkyl, preferably phenyl-$C_{1-2}$alkyl, wherein any alkyl is optionally substituted with one or more $R_6$ groups and any aryl is optionally substituted with one or more $R_7$ groups.

In another embodiment, the invention relates to compounds of formula I wherein $R_4$ represents aryl-$C_{1-2}$ alkyl, preferably phenyl-$C_{1-2}$alkyl, wherein any alkyl is optionally substituted with one or more $R_6$ groups and any aryl is optionally substituted with one or more $R_7$ groups; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein $R_4$ represents aryl, preferably phenyl, wherein any aryl is optionally substituted with one or more $R_7$ groups.

In another embodiment, the invention relates to compounds of formula I wherein each $R_6$ independently represents $C_{1-8}$alkyl; and optionally two $R_6$ groups on the same carbon atom are bonded together to form a —$C_{2-5}$ alkylene- group which is optionally substituted with one or more $C_{1-8}$alkyl groups.

In another embodiment, the invention relates to compounds of formula I wherein each $R_6$ independently represents $C_{1-8}$alkyl.

In another embodiment, the invention relates to compounds of formula I wherein two $R_6$ groups on the same carbon atom are bonded together to form a —$C_{2-5}$alkylene- group which is optionally Substituted with one or more $C_{1-8}$alkyl groups.

In another embodiment, the invention relates to compounds of formula I wherein each $R_7$ independently represents $C_{1-8}$alkyl, halo$C_{1-6}$alkyl, halogen, $C_{1-6}$alkoxy, halo$C_{1-6}$ alkoxy, —CN, hydroxy$C_{0-6}$alkyl, $CO_2R_9$—$C_{0-6}$alkyl, aryl or heteroaryl; wherein the aryl or heteroaryl groups in $R_7$ are optionally substituted with one or more $C_{1-8}$alkyl groups.

In another embodiment, the invention relates to compounds of formula I wherein each $R_7$ independently represents $C_{1-8}$ is alkyl.

In another embodiment, the invention relates to compounds of formula I wherein each $R_9$ independently represents H or $C_{1-8}$alkyl.

In another embodiment, the invention relates to compounds of formula I wherein n is 1; and $R_5$ is H.

In another embodiment, the invention relates to compounds of formula I wherein n is 1; $R_3$ is H or methyl; and $R_5$ is H.

In another embodiment, the invention relates to compounds of formula I wherein n is 1; $R_3$ is H; and $R_5$ is H.

In another embodiment, the invention relates to compounds of formula I wherein $R_3$ is H; and $R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$, alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups.

In another embodiment, the invention relates to compounds of formula I wherein $R_3$ is H;

$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_5$ groups, any cycloalkyl is optionally substituted with one or more substituents independently selected from $C_{1-8}$alkyl and halogen, and any aryl is optionally substituted with one or more $R_7$ groups; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein $R_3$ is H; and
$R_4$ represents $C_{1-8}$alkyl, preferably $C_{3-8}$alkyl.

In another embodiment, the invention relates to compounds of formula I wherein $R_3$ is H; and
$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen.

In another embodiment, the invention relates to compounds of formula I wherein $R_3$ is H; and $R_4$ represents $C_{3-10}$cycloalkyl-$C_{0-4}$alkyl, preferably $C_{3-10}$cycloalkyl-$C_{0-1}$ alkyl, and more preferably $C_{3-6}$cycloalkyl-$C_{0-1}$alkyl.

In another embodiment, the invention relates to compounds of formula I wherein $R_3$ is H; and $R_4$ represents $C_{3-10}$cycloalkyl-$C_1$alkyl, preferably $C_{3-6}$cycloalkyl-$C_1$alkyl, more preferably cyclopropylmethyl, wherein any alkyl is optionally substituted with one or more $R_6$ groups and any cycloalkyl is optionally substituted with one or more substituents independently selected from $C_{1-8}$alkyl and halogen.

In another embodiment, the invention relates to compounds of formula I wherein $R_3$ is H; and $R_4$ represents $C_{3-10}$cycloalkyl-$C_1$alkyl, preferably $C_{3-6}$cycloalkyl-$C_1$alkyl, more preferably cyclopropylmethyl.

In another embodiment, the invention relates to compounds of formula I wherein $R_3$ is H; and $R_4$ represents $C_{3-10}$cycloalkyl, preferably $C_{3-6}$cycloalkyl and more preferably cyclopentyl, wherein any cycloalkyl is optionally substituted with one or more substituents independently selected from $C_{1-8}$alkyl and halogen.

In another embodiment, the invention relates to compounds of formula I wherein $R_3$ is H; and $R_4$ represents $C_{3-10}$cycloalkyl, preferably $C_{3-6}$cycloalkyl and more preferably cyclopentyl.

In another embodiment, the invention relates to compounds of formula I wherein n is 1;
$R_3$ is H; and
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups.

In another embodiment, the invention relates to compounds of formula I wherein n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein n is 1;
$R_3$ is H; and
$R_4$ represents $C_{1-8}$alkyl, preferably $C_{3-8}$alkyl.

In another embodiment, the invention relates to compounds of formula I wherein n is 1;
$R_3$ is H; and
$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen.

In another embodiment, the invention relates to compounds of formula I wherein n is 1; $R_3$ is H; and $R_4$ represents $C_{3-10}$cycloalkyl-$C_{0-4}$alkyl, preferably $C_{3-10}$cycloalkyl-$C_{0-1}$ alkyl, and more preferably $C_{3-6}$cycloalkyl-$C_{0-1}$ alkyl.

In another embodiment, the invention relates to compounds of formula I wherein n is 1; $R_3$ is H; and $R_4$ represents $C_{3-10}$cycloalkyl-$C_1$alkyl, preferably $C_{3-6}$cycloalkyl-$C_1$alkyl, more preferably cyclopropylmethyl, wherein any alkyl is optionally substituted with one or more $R_6$ groups and any cycloalkyl is optionally substituted with one or more substituents independently selected from $C_{1-8}$alkyl and halogen.

In another embodiment, the invention relates to compounds of formula I wherein n is 1; $R_3$ is H; and $R_4$ represents $C_{3-10}$cycloalkyl-$C_1$alkyl, preferably $C_{3-6}$cycloalkyl-$C_1$alkyl, more preferably cyclopropylmethyl.

In another embodiment, the invention relates to compounds of formula I wherein n is 1; $R_3$ is H; and $R_4$ represents $C_{3-10}$cycloalkyl, preferably $C_{3-6}$cycloalkyl and more preferably cyclopentyl, wherein any cycloalkyl is optionally substituted with one or more substituents independently selected from $C_{1-8}$alkyl and halogen.

In another embodiment, the invention relates to compounds of formula I wherein n is 1; $R_3$ is H; and $R_4$ represents $C_{3-10}$cycloalkyl, preferably $C_{3-6}$cycloalkyl and more preferably cyclopentyl.

In another embodiment, the invention relates to compounds of formula I wherein n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_5$ groups, any cycloalkyl is optionally substituted with one or more substituents independently selected from $C_{1-8}$alkyl and halogen, and any aryl is optionally substituted with one or more $R_7$ groups; and
$R_5$ is H.

In another embodiment, the invention relates to compounds of formula I wherein n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_5$ groups, any cycloalkyl is optionally substituted with one or more substituents independently selected from $C_{1-8}$alkyl and halogen, and any aryl is optionally substituted with one or more $R_7$ groups;

$R_5$ is H; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein n is 1;

$R_3$ is H or methyl, preferably H;

$R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$alkyl and halogen; and $R_5$ is H.

In another embodiment, the invention relates to compounds of formula I wherein n is 1;

$R_3$ is H or methyl, preferably H;

$R_4$ represents $C_{3-8}$alkyl optionally substituted with one or more halogen or $C_{3-5}$cycloalkyl-$C_{0-1}$alkyl, wherein in the $C_{3-5}$cycloalkyl-$C_{0-1}$alkyl group the cycloalkyl group is optionally substituted with one or more substituents independently selected from $C_{1-6}$alkyl and halogen; and $R_5$ is H.

In another embodiment, the invention relates to compounds of formula I wherein n is 1;

$R_3$ is H;

$R_4$ represents $C_{1-8}$alkyl, preferably $C_{3-8}$alkyl; and $R_5$ is H.

In another embodiment, the invention relates to compounds of formula I wherein n is 1;

$R_3$ is H or methyl, preferably H;

$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen; and $R_5$ is H.

In another embodiment, the invention relates to compounds of formula I wherein n is 1;

$R_3$ is H;

$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_5$ groups and any cycloalkyl is optionally substituted with one or more substituents independently selected from $C_{1-8}$alkyl and halogen;

$R_5$ is H; and each $R_6$ independently represents $C_{1-8}$alkyl; and optionally two $R_6$ groups on the same carbon atom are bonded together to form a —$C_{2-5}$alkylene- group which is optionally substituted with one or more $C_{1-8}$alkyl groups.

In another embodiment, the invention relates to compounds of formula I wherein n is 1;

$R_3$ is H or methyl, preferably H;

$R_4$ represents $C_{3-6}$cycloalkyl-$C_{0-1}$alkyl, wherein the cycloalkyl is optionally substituted with one or more substituents independently selected from $C_{1-8}$alkyl and halogen; and $R_5$ is H.

In another embodiment, the invention relates to compounds of formula I wherein n is 1; $R_3$ is H or methyl; $R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$ alkyl; and $R_5$ is H.

In another embodiment, the invention relates to compounds of formula I wherein n is 1; $R_3$ is H; $R_4$ represents $C_{3-10}$cycloalkyl-$C_{0-4}$alkyl, preferably $C_{3-10}$cycloalkyl-$C_{0-1}$ alkyl, and more preferably $C_{3-6}$cycloalkyl-$C_{0-1}$ alkyl; and $R_5$ is H.

In another embodiment, the invention relates to compounds of formula I wherein n is 1; $R_3$ is H; $R_4$ represents $C_{3-10}$cycloalkyl-$C_1$alkyl, preferably $C_{3-6}$cycloalkyl-$C_1$alkyl, more preferably cyclopropylmethyl, wherein any alkyl is optionally substituted with one or more $R_6$ groups and any cycloalkyl is optionally substituted with one or more substituents independently selected from $C_{1-8}$alkyl and halogen; and $R_5$ is H.

In another embodiment, the invention relates to compounds of formula I wherein n is 1; $R_3$ is H or methyl; $R_4$ represents $C_{3-10}$cycloalkyl-$C_1$alkyl, preferably $C_{3-6}$cycloalkyl-$C_1$alkyl, more preferably cyclopropylmethyl; and $R_5$ is H.

In another embodiment, the invention relates to compounds of formula I wherein n is 1; $R_3$ is H; $R_4$ represents $C_{3-10}$cycloalkyl-$C_{0-4}$alkyl, preferably $C_{3-6}$cycloalkyl-$C_1$alkyl, more preferably cyclopropylmethyl; and $R_5$ is H.

In another embodiment, the invention relates to compounds of formula I wherein n is 1; $R_3$ is H or methyl, preferably H; $R_4$ represents $C_{3-10}$cycloalkyl, preferably $C_{3-6}$cycloalkyl and more preferably cyclopentyl, wherein any cycloalkyl is optionally substituted with one or more substituents independently selected from $C_{1-8}$alkyl and halogen; and $R_5$ is H.

In another embodiment, the invention relates to compounds of formula I wherein n is 1; $R_3$ is H or methyl; $R_4$ represents $C_{3-10}$cycloalkyl, preferably $C_{3-6}$cycloalkyl, more preferably cyclopentyl; and $R_5$ is H.

In another embodiment, the invention relates to compounds of formula I wherein n is 1; $R_3$ is H; $R_4$ represents $C_{3-10}$cycloalkyl, preferably $C_{3-6}$cycloalkyl and more preferably cyclopentyl; and $R_5$ is H.

In another embodiment, the invention relates to compounds of formula I wherein:

$R_1$ and $R_2$ form, together with the N atom to which they are bound, a saturated heterocyclic group selected from:

(i) a heterocyclic group which contains 2 N atoms and does not contain any other heteroatom, wherein said heterocyclic group is optionally substituted with one or more $C_{1-4}$alkyl groups; and (ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;

wherein said heterocyclic groups (i) and (ii) are 4- to 7-membered monocyclic, 7- to 8-membered bridged bicyclic or 8- to 12-membered fused bicyclic;

n is 1;

$R_3$ is H; and $R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;

$R_3$ is H; and $R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H; and
$R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H; and
$R_5$ is H.

In another embodiment, the invention relates to compounds of formula I wherein:

$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more $C_{1-4}$alkyl groups; and
(ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;
wherein said heterocyclic groups (i) and (ii) are 4- to 7-membered monocyclic, 7- to 8-membered bridged bicyclic or 8- to 12-membered fused bicyclic;

n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-6}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-6}$alkyl and halogen, and any aryl is optionally substituted with one or more $R_7$ groups; and
$R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups; and
$R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups; and
$R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{1-8}$alkyl, $C_{3-10}$cycloalkyl-$C_{0-4}$alkyl or aryl-$C_{0-4}$alkyl, preferably $C_{3-8}$alkyl, $C_{3-10}$cycloalkyl-$C_{0-1}$ alkyl or aryl-$C_{0-2}$alkyl, wherein in the $C_{3-10}$cycloalkyl-$C_{0-4}$alkyl, aryl-$C_{0-4}$alkyl, $C_{3-10}$cycloalkyl-$C_{0-1}$alkyl and aryl-$C_{0-2}$ alkyl groups any alkyl is optionally substituted with one or more $R_6$ groups, any cycloalkyl is optionally substituted with one or more substituents independently selected from $C_{1-8}$alkyl and halogen, and any aryl is optionally substituted with one or more $R_7$ groups; and
$R_5$ is H.

In another embodiment, the invention relates to compounds of formula I wherein:

$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more $C_{1-4}$alkyl groups; and (ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;

wherein said heterocyclic groups (i) and (ii) are 4- to 7-membered monocyclic, 7- to 8-membered bridged bicyclic or 8- to 12-membered fused bicyclic;

n is 1;

$R_3$ is H;

$R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$alkyl and halogen, and preferably $R_4$ represents $C_{3-6}$alkyl optionally substituted with one or more halogen or $C_{3-6}$cycloalkyl-$C_{0-1}$alkyl, wherein in the $C_{3-6}$cycloalkyl-$C_{0-1}$alkyl group the cycloalkyl group is optionally substituted with one or more substituents independently selected from $C_{1-8}$alkyl and halogen; and $R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;

$R_3$ is H;

$R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$alkyl and halogen, and preferably $R_4$ represents $C_{3-8}$alkyl optionally substituted with one or more halogen or $C_{3-6}$cycloalkyl-$C_{0-1}$alkyl, wherein in the $C_{3-6}$cycloalkyl-$C_{0-1}$alkyl group the cycloalkyl group is optionally substituted with one or more substituents independently selected from $C_{1-8}$alkyl and halogen; and $R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_b$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;

$R_3$ is H;

$R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$alkyl and halogen, and preferably $R_4$ represents $C_{3-8}$alkyl optionally substituted with one or more halogen or $C_{3-6}$cycloalkyl-$C_{0-1}$alkyl, wherein in the $C_{3-6}$cycloalkyl-$C_{0-1}$alkyl group the cycloalkyl group is optionally substituted with one or more substituents independently selected from $C_{1-8}$alkyl and halogen; and $R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;

$R_3$ is H;

$R_4$ represents $C_{1-8}$alkyl optionally substituted with one or more halogen or $C_{3-10}$cycloalkyl-$C_{0-4}$alkyl, wherein in the $C_{3-10}$cycloalkyl-$C_{0-4}$alkyl group the cycloalkyl group is optionally substituted with one or more substituents independently selected from $C_{1-8}$alkyl and halogen, and preferably $R_4$ represents $C_{3-8}$alkyl optionally substituted with one or more halogen or $C_{3-6}$cycloalkyl-$C_{0-1}$alkyl, wherein in the $C_{3-6}$cycloalkyl-$C_{0-1}$alkyl group the cycloalkyl group is optionally substituted with one or more substituents independently selected from $C_{1-8}$alkyl and halogen; and $R_5$ is H.

In another embodiment, the invention relates to compounds of formula I wherein:

$R_1$ and $R_2$ form, together with the N atom to which they are bound, a saturated heterocyclic group selected from:

(i) a heterocyclic group which contains 2 N atoms and does not contain any other heteroatom, wherein said heterocyclic group is optionally substituted with one or more $C_{1-4}$alkyl groups; and (ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;

wherein said heterocyclic groups (i) and (ii) are 4- to 7-membered monocyclic, 7- to 8-membered bridged bicyclic or 8- to 12-membered fused bicyclic;

n is 1;

$R_3$ is H;

$R_4$ represents $C_{1-8}$alkyl, preferably $C_{3-8}$alkyl; and $R_5$ is

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;

$R_3$ is H;

$R_4$ represents $C_{1-6}$alkyl, preferably $C_{3-8}$alkyl; and $R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{1-8}$alkyl, preferably $C_{3-8}$alkyl; and
$R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{1-8}$alkyl, preferably $C_{3-8}$alkyl; and
$R_5$ is H.

In another embodiment, the invention relates to compounds of formula I wherein:

$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more $C_{1-4}$alkyl groups; and
(ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;
wherein said heterocyclic groups (i) and (ii) are 4- to 7-membered monocyclic, 7- to 8-membered bridged bicyclic or 8- to 12-membered fused bicyclic;

n is 1;
$R_3$ is H;
$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen; and
$R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;
$R_3$ is H;

$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen; and
$R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_6$ groups and any cycloalkyl is optionally substituted with one or more substituents independently selected from $C_{1-8}$alkyl and halogen; and
$R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;
$R_3$ is H;
$R_4$ represents $C_{3-10}$cycloalkyl-$C_{0-4}$alkyl, preferably $C_{3-10}$cycloalkyl-$C_{0-1}$alkyl, and more preferably $C_{3-6}$cycloalkyl-$C_{0-1}$alkyl, wherein any alkyl is optionally substituted with one or more $R_3$ groups and any cycloalkyl is optionally substituted with one or more substituents independently selected from $C_{1-8}$alkyl and halogen; and
$R_5$ is H.

In another embodiment, the invention relates to compounds of formula I wherein:

$R_1$ and $R_2$ form, together with the N atom to which they are bound, a saturated heterocyclic group selected from:
(i) a heterocyclic group which contains 2 N atoms and does not contain any other heteroatom, wherein said heterocyclic group is optionally substituted with one or more Cu alkyl groups; and
(ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;
wherein said heterocyclic groups (i) and (ii) are 4- to 7-membered monocytic, 7- to 8-membered bridged bicyclic or 8- to 12-membered fused bicyclic;

n is 1;

$R_3$ is H;

$R_4$ represents $C_{3-10}$cycloalkyl-$C_1$alkyl, preferably $C_{3-6}$cycloalkyl-$C_1$alkyl, more preferably cyclopropylmethyl; and $R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;

$R_3$ is H;

$R_4$ represents $C_{3-10}$cycloalkyl-$C_1$alkyl, preferably $C_1$cycloalkyl-$C_1$alkyl, more preferably cyclopropylmethyl; and $R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_b$ represents H and particularly preferably $R_a$ represents H, $R_b$ represents methyl and $R_c$ represents H;

n is 1;

$R_3$ is H;

$R_4$ represents $C_{3-10}$cycloalkyl-$C_1$alkyl, preferably $C_{3-6}$cycloalkyl-$C_1$alkyl, cyclopropylmethyl; and $R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;

$R_3$ is H;

$R_4$ represents $C_{3-10}$cycloalkyl-$C_1$alkyl, preferably $C_{3-6}$cycloalkyl-$C_1$alkyl, more preferably cyclopropylmethyl; and $R_5$ is H.

In another embodiment, the invention relates to compounds of formula I wherein:

$R_1$ and $R_2$ form, together with the N atom to which they are bound, a saturated heterocyclic group selected from:

(i) a heterocyclic group which contains 2 N atoms and does not contain any other heteroatom, wherein said heterocyclic group is optionally substituted with one or more $C_{1-4}$alkyl-groups; and (ii) a heterocyclic group which contains 1 N atom and does not contain any other heteroatom, wherein said heterocyclic group is substituted with one —$NR_aR_b$ group and is optionally substituted with one or more $C_{1-4}$alkyl groups;

wherein said heterocyclic groups (i) and (ii) are 4- to 7-membered monocyclic, 7- to 8-membered bridged bicyclic or 8- to 12-membered fused bicyclic;

n is 1;

$R_3$ is H;

$R_4$ represents $C_{3-10}$cycloalkyl, preferably $C_{3-6}$cycloalkyl and more preferably cyclopentyl; and $R_5$ is H.

In another embodiment, the invention relates to compounds of formula I wherein:

$R_1$ and $R_2$ form, together with the N atom to which they are bound, a saturated heterocyclic group which contains 1 N atom and does not contain any other heteroatom, wherein said heterocyclic group is substituted with one —$NR_aR_b$ group and is optionally substituted with one or more $C_{1-4}$alkyl groups; wherein said heterocyclic group is 4- to 7-membered monocyclic, 7- to 8-membered bridged bicyclic or 8- to 12-membered fused bicyclic;

n is 1;

$R_3$ is H;

$R_4$ represents $C_{3-10}$cycloalkyl, preferably $C_{3-6}$cycloalkyl and more preferably cyclopentyl; and $R_5$ is H.

In another embodiment, the invention relates to compounds of formula I wherein:

$R_1$ and $R_2$ form, together with the N atom to which they are bound, a saturated heterocyclic group selected from (a) and (b), wherein $R_a$ and $R_b$ have the meaning described above for compounds of formula I and $R_c$ represents H or $C_{1-4}$alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;

$R_3$ is H;

$R_4$ represents $C_{3-10}$cycloalkyl, preferably $C_{3-6}$cycloalkyl and more preferably cyclopentyl; and $R_5$ is H.

In another embodiment, the invention relates to compounds of formula I wherein:

$R_1$ and $R_2$ form, together with the N atom to which they are bound, a saturated heterocyclic group of formula (a), wherein $R_a$ and $R_b$ have the meaning described above for compounds of formula I and $R_c$ represents H or $C_{1-4}$ alkyl, preferably $R_a$, $R_b$ and $R_c$ independently represent H or $C_{1-4}$alkyl, more preferably $R_a$, $R_b$ and $R_c$ independently represent H or methyl, still more preferably $R_a$ and $R_b$ independently represent H or methyl and $R_c$ represents H, even more preferably $R_a$ represents H, $R_b$ represents H or methyl and $R_c$ represents H and particularly preferably $R_a$ represents H, $R_b$ represents methyl and $R_c$ represents H;

n is 1;

$R_3$ is H;

$R_4$ represents $C_{3-10}$cycloalkyl, preferably $C_{3-6}$cycloalkyl and more preferably cyclopentyl; and $R_5$ is H.

Moreover, the present invention includes all possible combinations of the particular and preferred embodiments described above.

In an additional embodiment, the invention relates to a compound of formula I selected from the list of compounds of examples 1a-6j.

In a further embodiment, the invention relates to a compound of formula I selected from:
4-((Cyclopropylmethylamino)methyl)-6-(3-(methylamino)azetidin-1-yl)pyrimidin-2-amine;
4-((2-Adamantylamino)methyl)-6-(3-(methylamino)azetidin-1-yl)pyrimidin-2-amine;
4-(((2,2-Diethylcyclopropyl)methylamino)methyl)-6-(3-(methylamino)azetidin-1-yl)pyrimidin-2-amine;
4-((Cyclopentylamino)methyl)-6-(3-(methylamino)azetidin-1-yl)pyrimidin-2-amine;
4-(3-(Methylamino)azetidin-1-yl)-6-((pentylamino)methyl)pyrimidin-2-amine;
4-((Cyclopentyl(methyl)amino)methyl)-6-(3-(methylamino)azetidin-1-yl)pyrimidin-2-amine;
4-((Isobutylamino)methyl)-6-(3-(methylamino)azetidin-1-yl)pyrimidin-2-amine;
4-((Cyclopropytamino)methyl)-6-(3-(methylamino)azetidin-1-yl)pyrimidin-2-amine;
4-((tert-Butylamino)methyl)-6-(3-(methylamino)azetidin-1-yl)pyrimidin-2-amine;
4-((Isopropylamino)methyl)-6-(3-(methylamino)azetidin-1-yl)pyrimidin-2-amine;
4-(3-(methylamino)azetidin-1-yl)-6-((2,2,2-trifluoroethylamino)methyl)pyrimidin-2-amine;
4-(((1R,2R,4S)-bicyclo[2.2.1]heptan-2-ylamino)methyl)-6-(3-(methylamino)azetidin-1-yl)pyrimidin-2-amine;
(S)-4-((sec-butylamino)methyl)-6-(3-(methylamino)azetidin-1-yl)pyrimidin-2-amine; and
(R)-4-((sec-butylamino)methyl)-6-(3-(methylamino)azetidin-1-yl)pyrimidin-2-amine;
or a salt thereof.

In a further embodiment, the invention relates to a compound of formula (which is 4-((Cyclopropylmethylamino)methyl)-6-(3-(methylamino)azetidin-1-yl)pyrimidin-2-amine; or a salt thereof.

In a further embodiment, the invention relates to a compound of formula I which is 4-((2-Adamantylamino)methyl)-6-(3-(methylamino)azetidin-1-yl)pyrimidin-2-amine; or a salt thereof.

In a further embodiment, the invention relates to a compound of formula I which is 4-(((2,2-Diethylcyclopropyl)methylamino)methyl)-6-(3-(methylamino)azetidin-1-yl)pyrimidin-2-amine; or a salt thereof.

In a further embodiment, the invention relates to a compound of formula I which is 4-((Cyclopentylamino)methyl)-6-(3-(methylamino)azetidin-1-yl)pyrimidin-2-amine; or a salt thereof.

In a further embodiment, the invention relates to a compound of formula I which is 4-(3-(Methylamino)azetidin-1-yl)-6-((pentylamino)methyl)pyrimidin-2-amine; or a salt thereof.

In a further embodiment, the invention relates to a compound of formula I which is 4-((Cyclopentyl(methyl)amino)methyl)-6-(3-(methylamino)azetidin-1-yl)pyrimidin-2-amine; or a salt thereof.

In a further embodiment, the invention relates to a compound of formula I which is 4-((Isobutylamino)methyl)-6-(3-(methylamino)azetidin-1-yl)pyrimidin-2-amine; or a salt thereof.

In a further embodiment, the invention relates to a compound of formula I which is 4-((Cyclopropylamino)methyl)-6-(3-(methylamino)azetidin-1-yl)pyrimidin-2-amine; or a salt thereof.

In a further embodiment, the invention relates to a compound of formula I which is 4-((tert-Butylamino)methyl)-6-(3-(methylamino)azetidin-1-yl)pyrimidin-2-amine; or a salt thereof.

In a further embodiment, the invention relates to a compound of formula I which is 4-((Isopropylamino)methyl)-6-(3-(methylamino)azetidin-1-yl)pyrimidin-2-amine; or a salt thereof.

In a further embodiment, the invention relates to a compound of formula I which is 4-(3-(methylamino)azetidin-1-yl)-6-((2,2,2-trifluoroethylamino)methyl)pyrimidin-2-amine; or a salt thereof.

In a further embodiment, the invention relates to a compound of formula I which is 4-(((1R,2R,4S)-bicyclo[2.2.1]heptan-2-ylamino)methyl)-6-(3-(methylamino)azetidin-1-yl)pyrimidin-2-amine; or a salt thereof.

In a further embodiment, the invention relates to a compound of formula I which is (S)-4-((sec-butylamino)methyl)-6-(3-(methylamino)azetidin-1-yl)pyrimidin-2-amine; or a salt thereof.

In a further embodiment, the invention relates to a compound of formula I which is (R)-4-((sec-butylamino)methyl)-6-(3-(methylamino)azetidin-1-yl)pyrimidin-2-amine; or a salt thereof.

In an additional embodiment, the invention relates to compounds according to formula I which provide more than 50% inhibition of $H_4$ receptor activity at 10 μM, more preferably at 1 μM and even more preferably at 0.1 μM, in a $H_4$ receptor assay such as the one described in examples 7 or 8.

The compounds of the present invention contain one or more basic nitrogens and may, therefore, form salts with organic or inorganic acids. Examples of these salts include: salts with inorganic acids such as hydrochloric acid, hydrobromic acid, hydroiodic acid, nitric acid, perchloric acid, sulfuric acid or phosphoric acid; and salts with organic acids such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, among others. The compounds of the present invention may contain one or more acidic protons and, therefore, they may also form salts with bases, which also form part of the present invention. Examples of these salts include: salts with inorganic cations such as sodium, potassium, calcium, magnesium, lithium, aluminium, zinc, etc; and salts formed with pharmaceutically acceptable amines such as ammonia, alkylamines, hydroxylalkylamines, lysine, arginine, N-methylglucamine, procaine and the like.

There is no limitation on the type of salt that can be used, provided that these are pharmaceutically acceptable when used for therapeutic purposes. The term pharmaceutically acceptable salt refers to those salts which are, according to medical judgement, suitable for use in contact with the tissues of humans and other mammals without undue toxicity, irritation, allergic response and the like. Pharmaceutically acceptable salts are well known in the art.

The salts of a compound of formula I can be obtained during the final isolation and purification of the compounds of the invention or can be prepared by treating a compound of formula I with a sufficient amount of the desired acid (or base) to give the salt in a conventional manner. The salts of the compounds of formula I can be converted into other salts of the compounds of formula I by km exchange using ion exchange resins.

The compounds of formula I and their salts may differ in some physical properties but they are equivalent for the purposes of the present invention. All salts of the compounds of formula I are included within the scope of the invention.

The compounds of the present invention may form complexes with solvents in which they are reacted or from which they are precipitated or crystallized. These complexes are known as solvates. As used herein, the term solvate refers to a complex of variable stoichiometry formed by a solute (a compound of formula I or a salt thereof) and a solvent. Examples of solvents include pharmaceutically acceptable solvents such as water, ethanol and the like. A complex with water is known as a hydrate. Solvates of compounds of the invention (or salts thereof), including hydrates, are included within the scope of the invention.

The compounds of formula I may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula I, including all polymorphic forms ("polymorphs") thereof, are included within the scope of the invention.

Some of the compounds of the present invention may exist as several optical isomers and/or several diastereoisomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on the products of formula I. Optically pure isomers can also be individually obtained using enantiospecific synthesis. The present invention covers all individual isomers as well as mixtures thereof (for example racemic mixtures or mixtures of diastereomers), whether obtained by synthesis or by physically mixing them.

The present invention further covers all unlabeled and isotopically labeled forms of the compounds of formula I.

The compounds of formula I can be obtained by following the processes described below. As it will be obvious to one skilled in the art, the exact method used to prepare a given compound may vary depending on its chemical structure. Moreover, in some of the processes described below it may be necessary or advisable to protect the reactive or labile groups with conventional protecting groups. Both the nature of these protecting groups and the procedures for their introduction or removal are well known in the art (see for example Greene T. W. and Wuts P. G. M, "Protective Groups in Organic Synthesis", John Wiley & Sons, 3rd edition, 1999). Unless otherwise stated, in the methods described below the meanings of the different substituents are the meanings described above with regard to a compound of formula I.

In general, compounds of formula I wherein n is 1 can be obtained by reacting a compound of formula II with a compound of formula III, as shown in the following scheme:

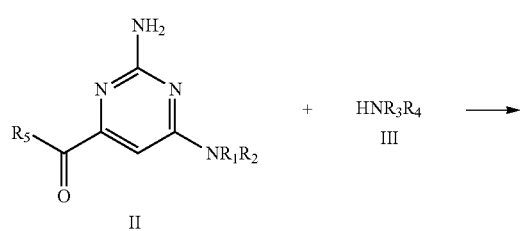

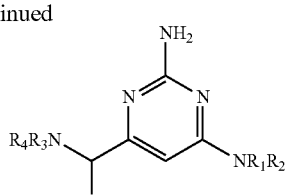

wherein $R_1$, $R_2$, $R_3$, $R_4$ and $R_5$ have the meaning described above with respect to a compound of formula I.

The reaction between the compounds of formulae II and III may be performed using a suitable reducing agent such as sodium cyanoborohydride and preferably sodium triacetoxyborohydride, optionally in the presence of an acid catalyst such as acetic acid and in a suitable solvent such as dichloromethane, dichloroethane, methanol or toluene, preferably dichloromethane, at a suitable temperature, usually at room temperature. Other suitable reducing agents include phenylsilane, in the presence of a catalyst such as dibutyltin dichloride and in a suitable solvent such as tetrahydrofuran, or hydrogen gas in the presence of a palladium catalyst.

The compounds of formula III are commercial or can be obtained by procedures described in the literature.

The compounds of formula II wherein n is 1 and $R_5$ is hydrogen (i.e compounds of formula IIa) can be obtained by oxidation of a compound of formula VI as shown in the following scheme:

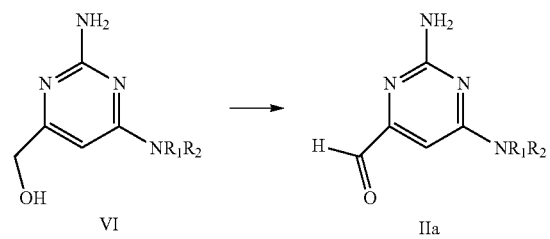

wherein $R_1$ and $R_2$ have the meaning described in formula I.

The reaction takes place by reacting the primary alcohol VI with an oxidizing agent such as oxalyl chloride/dimethylsulfoxide in dichloromethane and in the presence of triethylamine (Swern oxidation), manganese oxide in dichloromethane or tetrahydrofuran or, preferably, with sulfur trioxide pyridine complex in dimethylsulfoxide or dimethylsulfoxide-dichloromethane mixtures in the presence of an organic base such as triethylamine at a suitable temperature, usually at room temperature.

The amino substituents of the compounds of formula II and VI may be protected in order to prevent the formation of side products, if necessary. Any suitable amino-protective group may be used, such as for example a tert-butoxycarbonyl (Boc) group. A subsequent deprotection step may be necessary when the amino substituents of the compounds of formula II and/or VI are protected, which is carried out under standard conditions. When the protective group is Boc, the deprotection can be conducted by adding a solution of a strong acid such as HCl in a suitable solvent such as 1,4-dioxane, diethyl ether or methanol, or with trifluoroacetic acid in dichloromethane.

The compounds of formula VI can be obtained by reacting a compound of formula VII or VIIb with a compound of formula V, as shown in the following scheme:

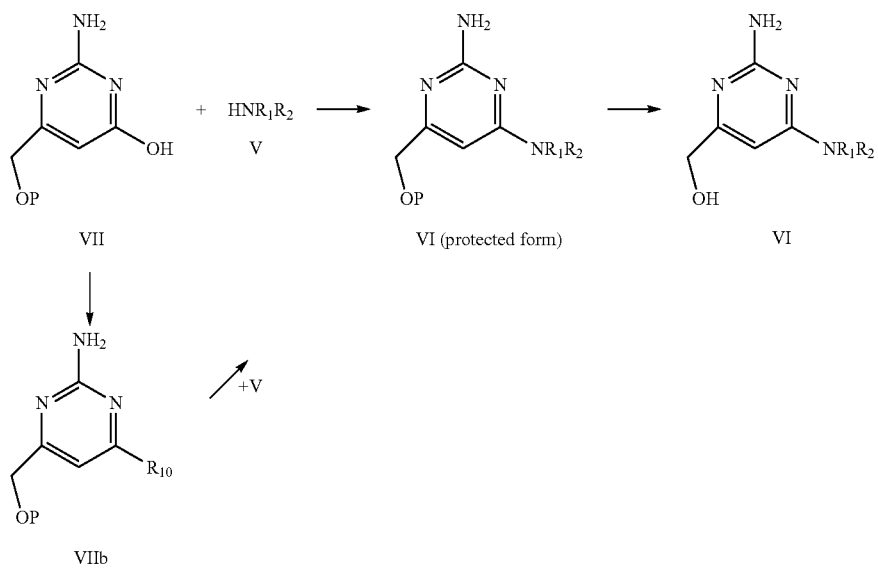

wherein $R_1$ and $R_2$ have the meaning described above with respect to a compound of formula I, $R_{10}$ represents a leaving group such as halogen (preferably chloro), mesylate, tosylate or triflate, and P represents a protecting group.

The reaction between the compounds of formulae VII and V may be performed using a coupling agent such as for example PyBOP (benzotriazol-1-yl-oxytripyrrolidinophosphonium hexafluorophosphate) in a suitable solvent such as 1,4-dioxane, tetrahydrofuran, dichloromethane, N,N-dimethylformamide, acetonitrile or mixtures thereof, preferably in acetonitrile or a mixture of acetonitrile/dioxane, in the presence of a base, such as N,N-diisopropylethylamine, dimethylaniline, diethylaniline, triethylamine or 1,8-diazabicyclo[5.4.0]undec-7-ene (DSU), preferably triethylamine. The reaction can be carried out at a temperature comprised between room temperature and the reflux temperature, preferably heating.

Alternatively the compounds of formula VI can be obtained by reacting a compound of formula V with a reactive derivative of a compound of formula VII (ie a compound VIIb) obtained by conversion of the hydroxy group present in a compound of formula VII into a leaving group such as halogen, mesylate, tosylate or triflate.

The —OH group from a compound of formula VII may be transformed into a leaving group such as halogen, preferably chloro, by reaction with a halogenating agent such as $POCl_3$, optionally in the presence of a suitable solvent, optionally in the presence of a base such as tetraethylammonium chloride, diisopropylethylamine or diethylaniline, among others; or with $POCl_3/PCl_5$ or N,N-dimethylformamide/oxalyl chloride mixtures in the presence of a suitable solvent such as 1,4-dioxane or 1,2-dichloroethane. The reaction is performed by heating, preferably at a temperature comprised between 50° C. and 100° C., preferably 70° C. The hydroxy group of a compound of formula VII can be transformed into a triflate group by reaction with trifluoromethanesulphonic anhydride in the presence of pyridine. The hydroxy group of a compound of formula VII can be transformed into a tosylate or mesylate group by reaction with p-toluenesulfonyl chloride or methanesulfonyl chloride in a suitable solvent such as dichloromethane in the presence of a base such as triethylamine or pyridine.

The reactive derivative of a compound of formula VII thus obtained (VIIb) is then allowed to react with a compound of formula V to give a compound of formula VI. The reaction is performed in a suitable solvent such as ethanol, methanol, butanol, N,N-dimethylformamide, dimethylsulphoxide, tetrahydrofuran, acetonitrile or toluene, in the presence of a base, including organic amines such as triethylamine, N,N-diisopropylethylamine, dimethylaniline and diethylaniline among others, and heating, preferably at a temperature comprised between 50 and 140° C. The heating may be thermal or by irradiating with microwaves at a wattage that allows to reach the temperature mentioned above.

In general, before conducting the reaction between the compounds of formula VII and V, or VIIb and V, the amino substituents of the compounds of formula V are protected in order to prevent the formation of side products. Similarly, the amino group of the compounds of formula VII and VIIb can also be protected if necessary. Any suitable amino-protective group may be used, such as for example a tert-butoxycarbonyl (Boc) group. A subsequent deprotection step may be necessary when the amino substituents of the compounds of formula VII and/or VIIb and/or V are protected, which is carried out under standard conditions. When the protective group is Boc, the deprotection can be conducted directly upon the crude product obtained by adding a solution of a strong acid such as HCl in a suitable solvent such as 1,4-dioxane, diethyl ether or methanol, or trifluoroacetic acid in dichloromethane.

The primary alcohol in starting materials VII and VIIb is also protected in a suitable form to carry out the reaction with the compound V. Any suitable alcohol-protective group may be used, such as for example a benzyl group. The subsequent deprotection step is performed under standard conditions.

The compounds of formula V are commercial or can be obtained by procedures described in the literature.

The compounds of formula VII can be obtained by reacting a compound of formula VIII with a guanidine source, preferably guanidine hydrochloride, as shown in the following scheme:

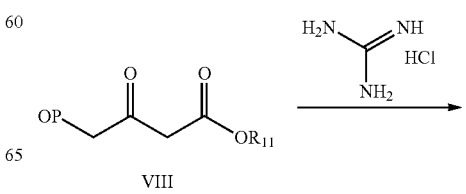

-continued

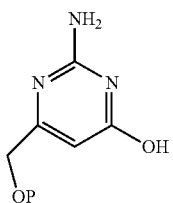

VII wherein $R_{11}$ represents methyl or ethyl.

The reaction takes place in the presence of a base such as potassium carbonate, sodium tert-butoxide or sodium ethoxide and preferably sodium methoxide, in a suitable solvent, preferably ethanol. The reaction can be performed by heating at a suitable temperature usually comprised between room temperature and the reflux temperature, preferably under reflux.

The compounds of formula VIII are commercial or can be easily obtained from commercial compounds by known methods.

Alternatively, the compounds of formula I wherein n is 1 and $R_5$ is hydrogen (i.e compounds of formula Ia) can be obtained from a compound of formula IV or a reactive derivative thereof (IVb) by reaction with a compound of formula V under similar conditions to those described for the transformation of VII and VIIb into VI, as shown in the following scheme:

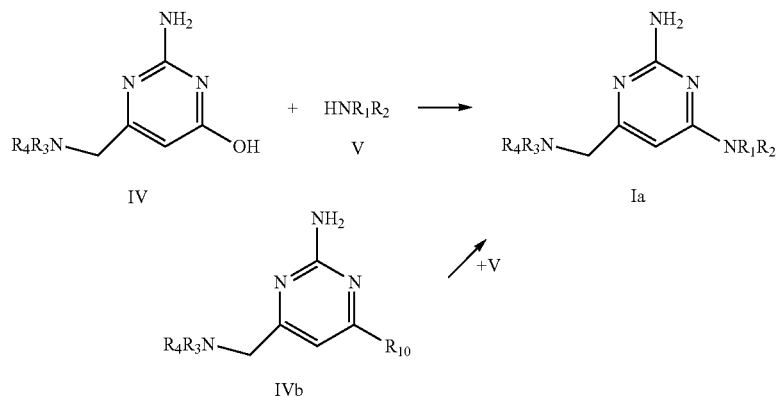

wherein $R_1$, $R_2$, $R_3$ and $R_4$ have the meaning described above with respect to a compound of formula I, and $R_{10}$ represents a leaving group such as halogen (preferably chloro), mesylate, tosylate or inflate.

The compounds of formula IV can be obtained by reacting a compound of formula IX with a guanidine source such as guanidine hydrochloride, under similar conditions previously disclosed for the preparation of a compound of formula VII, as shown in the following scheme:

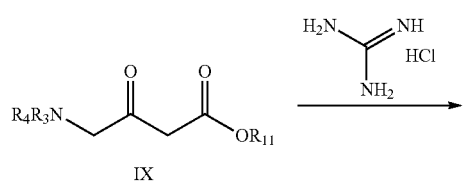

-continued

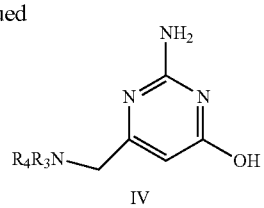

IV wherein $R_3$ and $R_4$ have the meaning described in formula I, and $R_{u1}$ represents methyl or ethyl.

The compounds of formula IX can be obtained by reacting a compound of formula X with an excess of a compound of formula III in a suitable solvent such as dichloromethane, as shown in the following scheme:

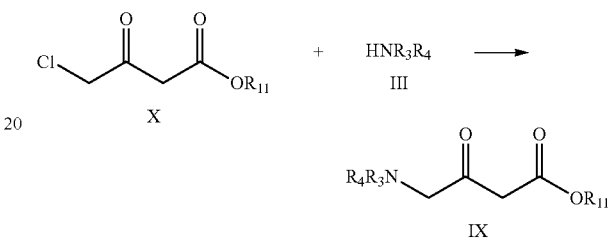

wherein $R_3$ and $R_4$ have the meaning described in formula I and $R_1$, represents methyl or ethyl.

The compounds of formula X are commercial or can be easily obtained from commercial compounds by known methods.

The compounds of formula IVb can obtained from a compound of formula IV by conversion of the —OH group into a leaving group, following the procedures described above for the conversion of VII to VIIb.

Alternatively, the compounds of formula II wherein n is 1 and $R_5$ is alkyl (i.e. compounds of formula IIb) can be prepared by reaction between compounds of formulae XI and XII as shown in the following scheme:

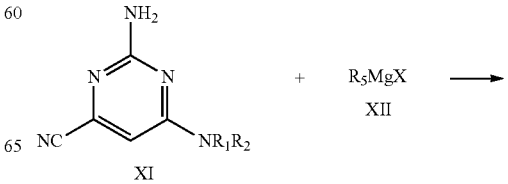

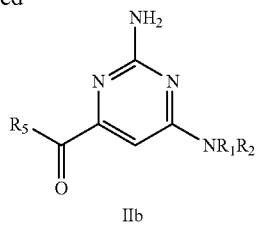

IIb wherein $R_1$ and $R_2$ have the meaning described in formula I, $R_5$ is alkyl, and X represents halogen, preferably iodo or bromo (see *Heterocycles* 2007, 71, 5, 1107).

The reaction can be carried out in a suitable solvent such as diethyl ether or tetrahydrofuran, at a suitable temperature, preferably room temperature.

The compounds of formula XI can be obtained by reacting a compound of formula XIII with a cyanide source such as $Zn(CN)_2$, as shown in the following scheme:

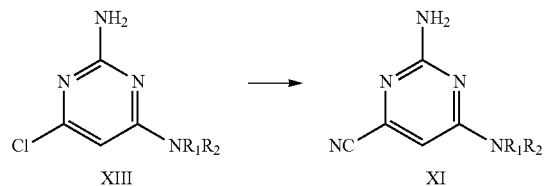

wherein $R_1$ and $R_2$ have the meaning described in formula I (see *Heterocycles* 2007, 71, 5, 1107).

The conversion of a compound of formula XIII to a compound of formula XI can be carried out by reacting XIII with a cyanide source such as zinc cyanide in the presence of a palladium catalyst such as tetrakis(triphenylphosphine)palladium(0) in a suitable solvent such as tetrahydrofuran, toluene and preferably in dimethylformamide or N-methylpyrrolidone and heating, preferably at 100° C.

Alternatively, compounds of formula IIb wherein $R_5$ represents methyl can be readily obtained by reacting a compound of formula XIII with tributyl(1-ethoxyvinyl)tin in the presence of a palladium catalyst such as tetrakis(triphenylphosphine)palladium(0), in the presence of a base such as potassium carbonate, in a suitable solvent such as tetrahydrofuran, toluene, dimethylformamide or dimethylacetamide and heating (see *Tetrahedron* 1997, 53, 6, 2291).

The compounds of formula XII are commercial or can be easily obtained from commercial compounds by known methods.

Other compounds of formula I (i.e compounds of formula Ic, which correspond to compounds of formula I wherein either n=1 and $R_5$ represents H, or n=2 and $(CR_5R_5)_2$ represents —($CH_2$)—($CR_5R_5$)—) can be obtained from a compound of formula XIV, as shown below:

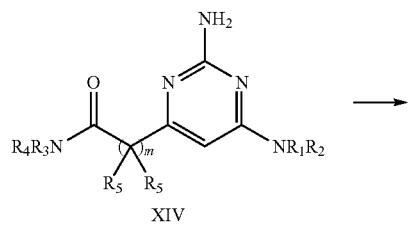

XIV

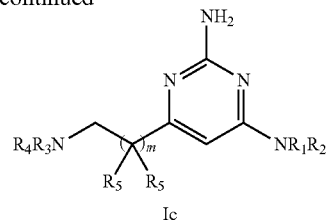

Ic wherein $R_1$, $R_2$, $R_3$, $R_4$ and $R_5$ have the meaning described in formula I, and m represents 0 or 1.

The reaction takes place in the presence of a reducing agent such as lithium aluminium hydride or borane in a suitable solvent such as tetrahydrofuran at a suitable temperature, comprised between room temperature and the reflux temperature.

Compounds of formula XIV, wherein m represents 0 (i.e compounds XIVa) can be obtained by reacting a compound of formula XV with compounds of formula III and V, as shown in the following scheme:

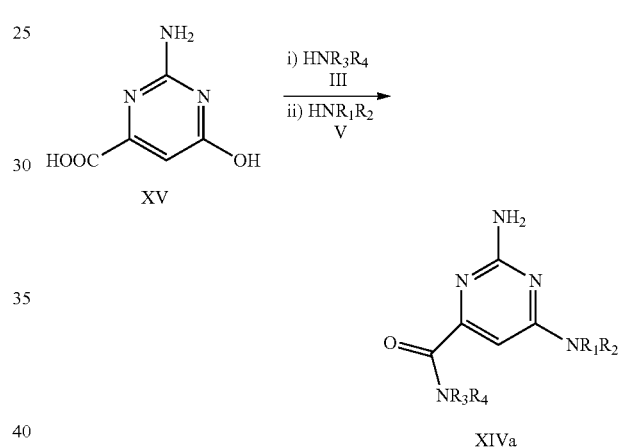

wherein $R_1$, $R_2$, $R_3$ and $R_4$ have the meaning described in formula I.

The reaction can be carried out by addition of the amine compound III and a coupling agent such as for example PyBOP (benzotriazol-1-yl-oxytripyrrolidinophosphonium hexafluorophosphate) or HBTU (O-benzotriazol-1-yl-N,N,N',N',-tetramethyluronium hexafluorophosphate), in a suitable solvent such as 1,4 dioxane, tetrahydrofuran, dichloromethane, N,N-dimethylformamide or acetonitrile in the presence of a base, such as N,N-diisopropylethylamine, dimethylaniline, diethylaniline, triethylamine or 1,8-diazabicyclo[5.4.0]undec-7-ene (DBU), followed by a second coupling step between the intermediate thus generated and the amine compound V using a coupling agent such as PyBOP under the coupling conditions described above for the reaction between III and XV. Alternatively, when PyBOP is used as the coupling agent, the reaction can be carried out in "one pot" by performing the second coupling step without isolation of the intermediate reaction product from XV and III. The reaction can be carried out at a temperature comprised between room temperature and the reflux temperature, preferably at room temperature for the first coupling step and preferably heating for the second coupling step.

The compound of formula XV is commercial.

Compounds of formula XIV, wherein m represents 1 (i.e compounds XIVb) can be obtained by reacting a compound of formula XVI with a compound of formula III as shown in the following scheme:

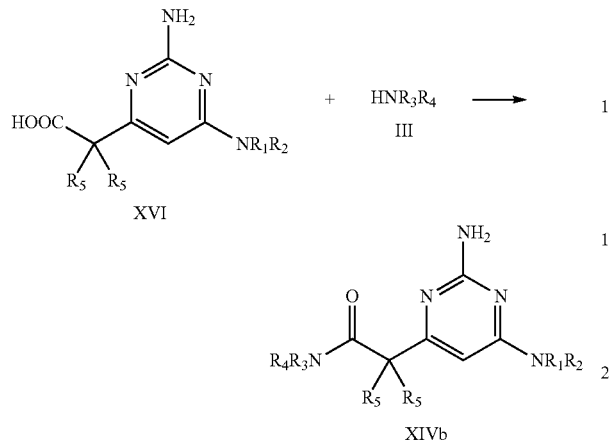

wherein $R_1$, $R_2$, $R_3$, $R_4$ and $R_5$ have the meaning described in general formula I.

The reaction between the compounds of formulae XVI and III may be performed using a coupling agent such as for example HBTU (O-benzotriazol-1-yl-N,N,N',N',-tetramethyluronium hexafluorophosphate) or PyBOP (benzotriazol-1-yl-oxytripyrrolidinophosphonium hexafluorophosphate) in a suitable solvent such as 1,4-dioxane, tetrahydrofuran, dichloromethane, acetonitrile, preferably in N,N-dimethylformamide, in the presence of a base, such as N,N-diisopropylethylamine, dimethylaniline, diethylaniline, triethylamine or 1,8-diazabicyclo[5.4.0]undec-7-ene (DBU), preferably triethylamine. The reaction can be carried out at a temperature comprised between room temperature and the reflux temperature, preferably room temperature.

The compounds of formula XVI can be obtained by hydrolysis of an ester compound of formula XVII under standard basic conditions, as shown in the following scheme:

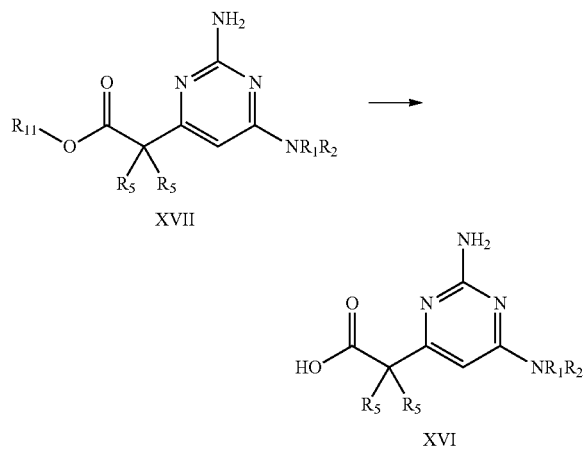

wherein $R_1$, $R_2$ and $R_5$ have the meaning described in formula I and $R_{11}$ represents methyl or ethyl.

The compounds of formula XVII can be prepared by reacting a compound of formula XVIII with a compound of formula V under similar conditions previously disclosed for the reaction between compounds of formulae VII and V, as shown in the following scheme:

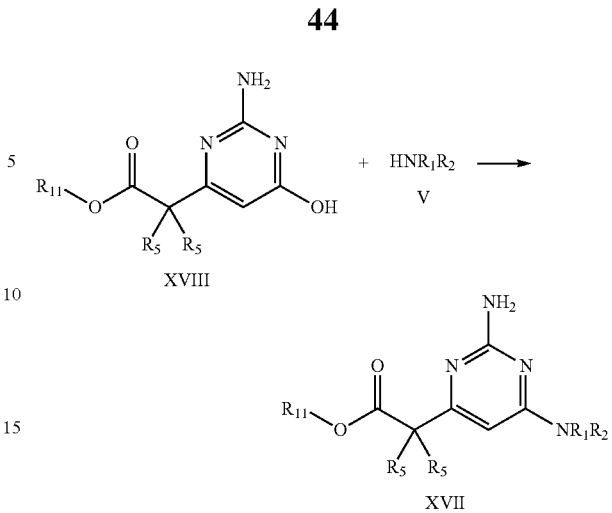

wherein $R_1$, $R_2$ and $R_5$ have the meaning described in formula I and $R_{11}$ represents methyl or ethyl.

The reaction of a compound of formula XIX with a guanidine source such as guanidine hydrochloride under similar conditions previously disclosed for the preparation of a compound of formula VII and IV gives rise to compounds of formula XVIII, as shown below:

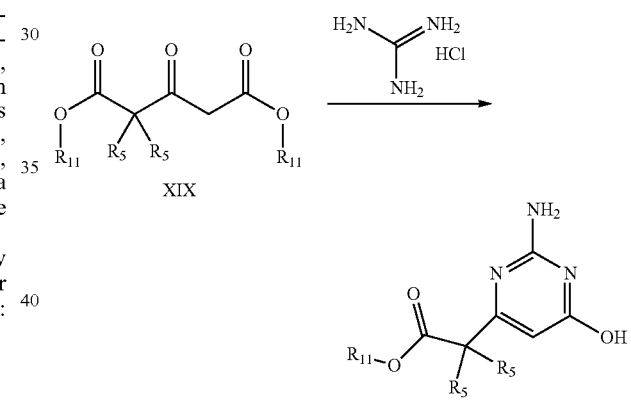

wherein $R_5$ has the meaning described in formula I and $R_{11}$ represents methyl or ethyl.

The compounds of formula XIX are commercial or can be easily obtained from commercial compounds by known methods.

Alternatively, compounds of formula I wherein n is 1 can be obtained by reacting a compound of formula XX with a compound of formula III, as shown in the following scheme:

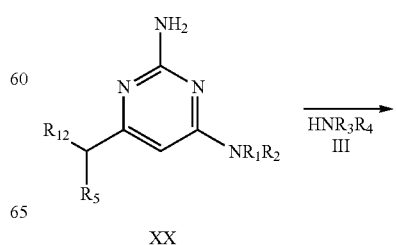

-continued

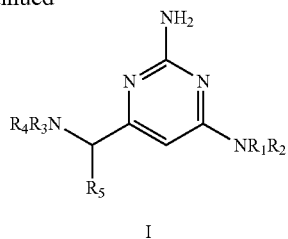

wherein $R_1$, $R_2$, $R_3$, $R_4$ and $R_5$ have the meaning described above with respect to a compound of formula I and $R_{12}$ represents a leaving group such as halogen, mesylate, tosylate or triflate.

The reaction of displacement between the compounds of formulae XX and III may be performed in the presence of a suitable base and solvent. The base can be an excess of III or alternatively a bulky tertiary amine such as diisopropylethylamine or dimethylaniline, among others. As suitable solvents, acetonitrile, dichloromethane, chloroform, tetrahydrofurane, or dioxane, among others, can be used. The reaction can be performed at a temperature comprised between room temperature and 100° C. with pressure or without.

The compounds of formula XX wherein $R_5$ is $C_{1-8}$alkyl can be obtained by reduction of ketone II (wherein $R_5$ is $C_{1-8}$ alkyl) to give compound XXI (wherein $R_5$ is $C_{1-8}$alkyl) followed by conversion of the —OH group of compound of formula XXI into a leaving group $R_{12}$. Similarly, the compounds of formula XX wherein $R_5$ is H can be obtained by transforming the —OH group of compound of formula VI into a leaving group $R_{12}$ as shown in the following scheme:

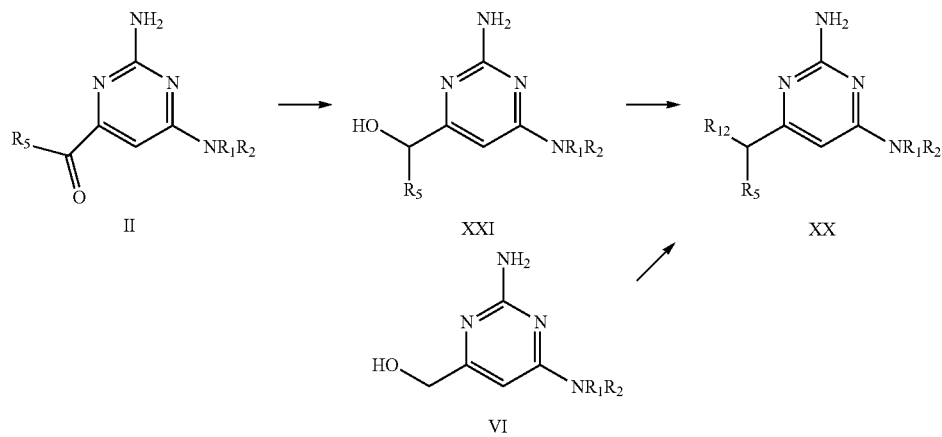

wherein $R_1$, $R_2$ and $R_5$ have the meaning described above with respect to a compound of formula I and $R_{12}$ represents a leaving group such as halogen, mesylate, tosylate or triflate.

The reaction of reduction of II to give XXI may be performed using a suitable reducing agent such as sodium borohydride, lithium aluminium hydride, selectride or borane in a suitable solvent such as tetrahydrofuran at a suitable temperature, comprised between room temperature and the reflux temperature.

The —OH group in compound XXI or VI may be transformed into a leaving group such as halogen, preferably chloro, by reaction with a halogenating agent such as thionyl chloride, in the presence of a suitable solvent such us tetrahydrofurane or dichloromethane, optionally in the presence of a base such pyridine; the —OH group in compound XXI or VI can be transformed into a triflate group by reaction with trifluoromethanesulphonic anhydride in the presence of pyridine or can be transformed into a tosylate or mesylate group by reaction with p-toluenesulfonyl chloride or methanesulfonyl chloride in a suitable solvent such as dichloromethane in the presence of a base such as triethylamine or pyridine.

Moreover, certain compounds of the present invention can also be obtained starting from other compounds of formula I by appropriate conversion reactions of functional groups, in one or several steps, using well-known reactions in organic chemistry under standard experimental conditions.

In general, before conducting any of the above reaction step wherein an amino group ($NH_2$) and/or an amino group in $NR_1R_2$ are present, it may be advisable to protect said groups with a suitable protecting group, preferably a Pert-butoxycarbonyl (Boc) group. If Boc is used, deprotection can be conducted directly upon the crude product obtained by adding a solution of a strong acid such as HCl in a suitable solvent such as 1,4-dioxane, diethyl ether or methanol, or trifluoroacetic acid in dichloromethane.

As previously mentioned, the compounds of the present invention show potent histamine $H_4$ receptor antagonist activity. Therefore, the compounds of the invention are expected to be useful to treat or prevent diseases mediated by the $H_4$ receptor in mammals, including human beings.

Diseases mediated by the $H_4$ receptor that can be treated or prevented with the compounds of the present invention include, among others, allergic, immunological or inflammatory diseases, pain or cancer.

Examples of allergic, immunological or inflammatory diseases that can be treated or prevented with the compounds of the invention include without limitation: respiratory diseases, such as asthma, allergic rhinitis and chronic obstructive pulmonary disease (COPD); ocular diseases, such as allergic rhinoconjunctivitis, dry eye and cataracts; skin diseases, such as eczema, dermatitis (e.g. atopic dermatitis), psoriasis, urticaria, pemphigus, dermatitis herpetiformis, cutaneous vasculitis and pruritus; inflammatory bowel diseases, such as ulcerative colitis and Crohn's disease; autoimmune diseases such as rheumatoid arthritis, multiple sclerosis, cutaneous lupus, systemic lupus erythematosus, and systemic vasculitis such as allergic vasculitis and periarteritis nodosa; and transplant rejection.

Examples of pain conditions that can be treated or prevented with the compounds of the invention include, among others, inflammatory pain, inflammatory hyperalgesia, hyperalgesia, post-surgical pain, migraine, cancer pain, visceral pain, osteoarthritis pain and neuropathic pain.

In a preferred embodiment, the compounds of the invention are used for the treatment or prevention of an allergic, immunological or inflammatory disease. In a more preferred embodiment, the compounds of the invention are used for the treatment or prevention of an allergic, immunological or inflammatory disease selected from a respiratory disease, an ocular disease, a skin disease, an inflammatory bowel disease, an autoimmune disease, and transplant rejection. In a still more preferred embodiment, the allergic, immunological or inflammatory disease is selected from asthma, allergic rhinitis, chronic obstructive pulmonary disease (COPD), allergic rhinoconjunctivitis, dry eye, cataracts, eczema, dermatitis (e.g. atopic dermatitis), psoriasis, urticaria, pemphigus, dermatitis herpetiformis, cutaneous vasculitis, pruritus, ulcerative colitis, Crohn's disease, rheumatoid arthritis, multiple sclerosis, cutaneous lupus, systemic lupus erythematosus, systemic vasculitis, and transplant rejection.

In another preferred embodiment, the compounds of the invention are used for the treatment or prevention of pain, preferably inflammatory pain, inflammatory hyperalgesia, hyperalgesia, post-surgical pain, migraine, cancer pain, visceral pain, osteoarthritis pain or neuropathic pain.

Assays to determine the ability of a compound to interact with the histamine $H_4$ receptor are well known in the art. For example, one can use a $H_4$ receptor binding assay such as the one explained in detail in example 7. Another useful assay is a GTP [$\beta$-$^{35}$S] binding assay to membranes that express the $H_4$ receptor. Functional assays with $H_4$ receptor-expressing cells can also be used, for example in a system measuring any kind of cellular activity mediated by a second messenger associated with the $H_4$ receptor, such as intracellular cAMP levels or $Ca^{2+}$ mobilization. In this regard, a very useful functional assay that can be used to determine anti-$H_4$ receptor activity is the Gated Autofluorescence Forward Scatter assay (GAFS) in eosinophils, for example human eosinophils, as disclosed in detail in example 8; this assay is well know in the art (see for example the method disclosed in Buckland K F et al, 2003, cited above in the Background section, which is incorporated herein by reference). In vivo assays that can be used to test the activity of the compounds of the invention are also well known in the art (see for example the various literature references listed for in vivo animal models in the Background section, particularly those relating to in vivo models of peritonitis, pleurisy, allergic asthma, inflammatory bowel disease, atopic dermatitis, pruritus and pain, which are all incorporated herein by reference). Other in vivo assays that can be used, particularly to test compounds administered topically, are the delayed type hypersensitivity to oxazolone assay (Tarayre, J P et al., Arzneimittel-Forschung, 40(10): 1125-1131 (1990), which is herein incorporated by reference) and a mice atopic dermatitis model by multiple oxazolone challenges such as the one disclosed in detail in example 10).

The selectivity profile of the compounds of the invention can be tested using standard histamine receptor binding assays using the various histamine receptors similarly to the one disclosed in example 7. In addition, to test the selectivity for other receptors or ion channels, displacement assays of the corresponding radioligands can be used following the standard procedures reported in the literature and well known in the art. To test the selectivity for enzymes, determination of enzymatic activity by product formation from its substrate can be used.

The toxicity and safety profile of the compounds of the invention can be determined using standard tests that are well known in the art. An assay that is indispensable in order to determine cardiac safety profile of a drug candidate is the assessment of inhibition of the hERG channel using a patch-clamp test, such as the one described in more detail in example 9. Other standard in vitro toxicity assays that can be carried out are: viability panel in different cell lines (i.e. HepG2, Jurkat, U937, A549, Hela, CHO-K1), Ames test, micronuclei assay, glutathione depletion, or drug induced phospholipidosis assay (Regarding in vivo toxicity, several tests can be performed: acute and repeated toxicity in rodents and other species for general toxicity, and Murine Local Lymph Node Assay (LLNA) and maximization test in guinea-pig for skin sensitization potential.

To be devoid of unwanted central nervous system effects, peripherally acting drugs must show limited ability to cross BBB. To test the ability to of a drug penetrate in CNS system, plasma/brain ratio after administration of drug can be determined.

For selecting active compounds, testing at 10 μM must result in an activity of more than 50% inhibition of $H_4$ receptor activity in the test provided in example 7. More preferably, compounds should exhibit more than 50% inhibition at 1 μM and still more preferably at 0.1 μM in this assay. Preferred compounds should also exhibit potent activity in the GAFS assay of example 8; preferably, compounds should exhibit more than 50% inhibition at 10 μM, more preferably at 1 μM and still more preferably at 0.1 μM in this assay.

Preferred compounds should exhibit selective affinity for the $H_4$ receptor over other receptors, particularly the $H_3$, muscarinic, adrenergic, dopamine and serotonine receptors, and over ion channels, particularly hERGK+ channel.

The compounds of the present invention exhibit advantageous properties. In addition to having potent activity as $H_4$ receptor modulators, compounds of the invention have been found to exhibit good cardiac safety profile in the Herg channel inhibition assay. Moreover, the compounds of examples 1b and 1t have been shown to exhibit outstanding in vivo activity in the atopic dermatitis model of example 10.

The present invention also relates to a pharmaceutical composition which comprises a compound of the invention (or a pharmaceutically acceptable salt or solvate thereof) and one or more pharmaceutically acceptable excipients. The excipients must be "acceptable" in the sense of being compatible with the other ingredients of the composition and not deleterious to the recipients thereof.

The compounds of the present invention can be administered in the form of any pharmaceutical formulation, the nature of which, as it is well known, will depend upon the nature of the active compound and its route of administration. Any route of administration may be used, for example oral, parenteral, nasal, ocular, topical and rectal administration. In a preferred embodiment, the compounds of the invention are administered orally. In another embodiment, the compounds of the invention are administered topically.

Solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogenphosphate; binding agents such as for example starch, gelatin or povidone; disintegrants such as sodium carboxymethyl starch or sodium croscarmellose; and lubricating agents such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, in which the active compound is mixed with water or an oily medium, for example coconut oil, mineral oil or olive oil.

Powders and granulates for the preparation of oral suspensions by the addition of water can be obtained by mixing the active compound with dispersing or wetting agents; suspending agents and preservatives. Other excipients can also be added, for example sweetening, flavouring and colouring agents.

Liquid forms for oral administration include emulsions, solutions, suspensions, syrups and elixirs containing commonly-used inert diluents, such as purified water, ethanol, sorbitol, glycerol, polyethylene glycols (macrogols) and propylene glycol Said compositions can also contain coadjuvants such as wetting, suspending, sweetening, flavouring agents, preservatives and buffers.

Injectable preparations, according to the present invention, for parenteral administration, comprise sterile solutions, suspensions or emulsions, in an aqueous or non-aqueous solvent such as propylene glycol, polyethylene glycol or vegetable oils. These compositions can also contain coadjuvants, such as wetting, emulsifying, dispersing agents and preservatives. They may be sterilized by any known method or prepared as sterile solid compositions which will be dissolved in water or any other sterile injectable medium immediately before use. It is also possible to start from sterile materials and keep them under these conditions throughout all the manufacturing process.

The compounds of the invention can also be formulated for their topical application for the treatment of pathologies occurring in zones or organs accessible through this route, such as eyes, skin and the intestinal tract. Formulations include creams, lotions, gels, powders, solutions and patches wherein the compound is dispersed or dissolved in suitable excipients.

For the nasal administration or for inhalation, the compound can be formulated as an aerosol, from which it can be conveniently released using suitable propellants.

The dosage and frequency of doses may be ascertained by routine methods such as modeling, dose escalation studies or clinical trials and by taking into account factors such as the nature and severity of the disease to be treated, the age, the general condition and body weight of the patient, as well as the particular compound administered, its pharmacokinetic profile, and the route of administration, among other factors. As an example, a suitable dosage range is from about 0.01 mg/Kg to about 100 mg/Kg per day, which can be administered as a single or divided doses.

The invention is illustrated by the following examples.

EXAMPLES

The following abbreviations are used in the examples:
AcN: acetonitrile
Bac: tertbutoxycarbonyl
conc: concentrate
DIPEA: diisopropylethylamine
DMSO: dimethylsulfoxide
EtOAc: ethyl acetate
EtOH: ethanol
MeOH: methanol
Min: minutes
TEA: triethylamine
THF: tetrahydrofuran
$t_R$: retention time
LC-MS: liquid chromatography-mass spectrometry One of the following methods was used to determine the LC-MS spectrums:
Method 1: X-Terra MS $C_{18}$ column 5 μm (100 mm×2.1 mm), temperature: 30° C., rate: 0.35 mL/min, eluent A=AcN, B=$NH_4HCO_3$ 10 mM, gradient: 0 min A at 10%; 10 min A at 90%; 15 mM A at 90%.
Method 2: Acquity HPLC BEH C18 column 1.7 μm (2.1×50 mm), temperature: 40° C., rate: 0.50 mL/min, eluent: A=AcN, B=$NH_4HCO_3$ 10 mM, gradient: 0 min A at 10%; 0.25 min A at 10%; 3.00 min A at 90%; 3.75 min A at 90%.

When indicated, the compounds were purified by preparative HPLC according to the following general method: X-Bridge Prep C18 columna 5 μm OBD (19×100 mm), flow: 20 mL/min, eluent: A=AcN, B=$NH_4HCO_3$ 75 mM, gradient: 0 min A at 5-10%; 9.0 min A at 95-90% (gradient was adapted when required to ensure proper purification).

Reference Example 1 tert-Butyl methyl[(3R)-pyrrolidin-3-yl]carbamate (a) tert-Butyl[(3R)-1-benzylpyrrolidin-3-yl]methylcarbamate Di-tert-butyl dicarbonate (11.6 g, 53.07 mmol) dissolved in 15 mL of $CH_2Cl_2$ was added to a solution of (3R)-1-benzyl-N-methylpyrrolidin-3-amine (10 g, 52.55 mmol) in 115 mL of $CH_2Cl_2$, cooled at 0° C. The resulting solution was stirred at room temperature for 18 hours. The solvent was evaporated and the crude product was chromatographed over silica gel using hexane/EtOAc mixtures of increasing polarity as eluent, providing 14.5 g of the desired compound (yield: 95%).
LC-MS (Method 1): $t_R$=9.55 min; m/z=291 ($MH^+$).

(b) Title Compound

A mixture of the compound obtained above (14.5 g, 50.14 mmol), Pd/C (10%, 50% in water) (3 g) and ammonium formate (12.7 g, 200.5 mmol) in MeOH (390 mL) and water (45 mL) was heated under reflux for 5 hours. The reaction mixture was filtered through Celite® and the filter was washed with EtOAc and MeOH. The solvent was evaporated to dryness, providing 10.6 g of the title compound as an oil (yield: 100%).
$^1$H NMR (300 MHz, $CDCl_3$) δ: 1.38 (s, 9H), 1.72 (m, 1H), 1.96 (m, 1H), 2.53 (s, NH), 2.80 (s, 3H), 2.87 (m, 1H), 2.93 (m, 1H), 3.11 (m, 2H), 4.58 (m, 1H).

Reference Example 2 tert-Butyl azetidin-3-yl(methyl)carbamate (a) tert-Butyl [1-(diphenylmethyl)azetidin-3-yl]methylcarbamate Following a procedure similar to that described in section a) of reference example 1, but using 1-(diphenylmethyl)-N-methylazetidin-3-amine instead of (3R)-1-benzyl-N-methylpyrrolidin-3-amine, the desired compound was obtained with a 73% yield.
LC-MS (Method 1): $t_R$=10.14 min; m/z=353 ($MH^+$).

(b) Title Compound

A solution of the compound obtained above (6.18 g, 17.53 mmol) in 60 mL of MeOH and 15 mL of EtOAc was purged with argon. Pd/C (10%, 50% in water) (929 mg) was added and the mixture was then purged again with argon and stirred in a $H_2$ atmosphere for 18 hours. The reaction was filtered through Celite® and the filter was washed with EtOAc and MeOH. The solvent was evaporated to dryness, providing 5.66 g of a mixture of the title compound together with one equivalent of diphenylmethane, that was used as such in the following steps.

$^1$H NMR (300 MHz, $CD_3OD$) δ: 1.44 (s, 9H), 2.88 (s, 3H), 3.56 (m, 2H), 3.71 (m, 2H), 4.75 (m, 1H).

Reference Example 3

Ethyl 4-(benzyloxy)-3-oxobutanoate

Benzyl alcohol (19.7 g, 182.3 mmol) was slowly added to a suspension of sodium hydride (15.9 g 55% in mineral oil, 364.5 mmol) in anhydrous diethyl ether (116 mL) and the resulting mixture was stirred at room temperature for 1 hour. It was then diluted with some diethyl ether to ensure good stirring. Ethyl 4-chloro-3-oxobutanoate (12.3 mL, 91.1 mmol) was then slowly added and the mixture was stirred at room temperature overnight. The reaction mixture was cooled with an ice bath and then diluted with cold water and diethyl ether pH was adjusted to 4 with 5 N HCl and it was extracted three times with diethyl ether containing some ethyl acetate. The combined organic phases were dried over $Na_2SO_4$ and it was concentrated to dryness, thus obtaining the title compound with quantitative yield as a crude product that was used as such in the following step.

LC-MS (Method 2): $t_R$=2.03 min; m/z=235 (MH$^-$).

Reference Example 4

2-Amino-6-(benzyloxymethyl)pyrimidin-4-ol

Guanidine hydrochloride (13.07 g, 136.7 mmol) and sodium methoxide (7.38 g, 136.7 mmol) were added to a solution of the crude compound obtained in reference example 3 (91.1 mmol, in theory) in absolute ethanol (580 mL) and the mixture was heated under reflux overnight. The solvent was evaporated to dryness. The residue was diluted with water and pH was, then, adjusted to 6 with aqueous HCl. The precipitated solids were collected by filtration, washed with a small amount of diethyl ether and dried in a vacuum oven, providing 17.9 g of the title compound (yield: 85%, from ethyl 4-chloro-3-oxobutanoate).

LC-MS (Method 2): $t_R$=1.25 min; m/z 232 (MH$^+$).

Reference Example 5

4-(Benzyloxymethyl)-6-chloropyrimidin-2-amine

Phosphorus oxychloride (28.6 mL, 312.6 mmol) was added to a mixture of the compound obtained in reference example 4 (7.23 g, 31.2 mmol) in 1,4-dioxane (115 mL) and the mixture was heated at 70° C. overnight. The POCl$_3$/dioxane mixture was distilled off. EtOAc was added and then stripped off and this operation was repeated twice more to ensure complete removal of phosphorus oxychloride. The residue was diluted with water and pH was adjusted to 7 with aqueous NaOH. EtOAc was then added and the phases were separated. The aqueous phase was extracted twice with ethyl acetate. The combined organic phases were dried over $Na_2SO_4$ and concentrated to dryness, thus obtaining 6.37 g of the title compound as a crude product that was used as such in the following step (yield: 81%)

LC-MS (Method 2): $t_R$=2.07 min; m/z=250/252 (MH$^+$).

Reference Example 6a (R)-tert-Butyl 1-(2-amino-6-(benzyloxymethyl)pyrimidin-4-yl)pyrrolidin-3-yl)methyl)carbamate A mixture of the compound obtained in reference example 5 (6.37 g, 25.5 mmol), the compound obtained in reference example 1 (5.11 g, 25.5 mmol) and DIPEA (4.4 mL, 25.5 mmol) in EtOH (64 mL) was heated at reflux overnight. The reaction mixture was evaporated to dryness and the residue was purified by chromatography over silica gel using mixtures of hexane/EtOAc of increasing polarity as eluent, providing 6.61 g of the title compound (yield: 63%).

LC-MS (Method 2): $t_R$=2.32 min; m/z 414 (MH$^+$).

Reference Example 6b tert-Butyl 1-(2-amino-6-(benzyloxymethyl)pyrimidin-4-yl)azetidin-3-yl(methyl)carbamate The title compound was obtained following a similar procedure to that described in reference example 6a but using reference example 5 and reference example 2 as starting materials.

LC-MS (Method 2): $t_R$=2.25 min; m/z 400 (MH$^+$).

Reference Example 7a tert-Butyl 1-(2-amino-6-(hydroxymethyl)pyrimidin-4-yl)azetidin-3-yl(methyl)carbamate A solution of ammonium formate (1.67 g, 26.5 mmol) in water (6.9 mL) was added to a mixture of the compound obtained in reference example 6b (5.3 g, 13.2 mmol) and Pd/C (10%, 50% in water) (0.52 g) in EtOH (390 mL) and the resulting mixture was heated under reflux for 3 hours. The reaction mixture was filtered through Celite® and the filter aid was washed with EtOH. The solvent was evaporated to dryness and the crude thus obtained was subjected to a second hydrogenation cycle, providing 3.97 g of the title compound (yield: 97%).

LC-MS (Method 2): $t_R$=1.38 min; m/z 310 (MH$^+$).

Reference Example 7b (R)-tert-Butyl 1-(2-amino-6-(hydroxymethyl)pyrimidin-4-yl)pyrrolidin-3-yl)methyl)carbamate The title compound was obtained following a similar procedure to that described in reference example 7a but using reference example 6a as starting material.

LC-MS (Method 2): $t_R$=1.55 min; m/z 324 (MH$^+$).

Reference Example 8a tert-Butyl 1-(2-amino-6-formylpyrimidin-4-yl)azetidin-3-yl(methyl)carbamate A solution of the compound obtained in reference example 7a (2 g, 6.46 mmol) in dichloromethane (51.5 mL) was cooled to 0° C. with an ice bath under an argon atmosphere. Triethylamine (2.7 mL, 19.4 mmol) was added and, finally, a solution of sulphur trioxide pyridine complex (3 g, 19.4 mmol) in DMSO (17.5 mL) was slowly added. The mixture was stirred at room temperature for 3 hours. It was again cooled to 0° C. and diluted with chloroform and ice. The phases were separated and the aqueous phase was extracted twice again with chloroform. The combined organic phases were washed with sodium bicarbonate saturated solution, dried over $Na_2SO_4$ and concentrated to dryness, thus obtaining 2.2 g of the title compound as a crude product that was used as such in the following step (quantitative yield)

LC-MS (Method 2): $t_R$=1.61 min (broad peak); m/z=308 (MH$^+$).

Reference Example 8b (R)-tert-Butyl 1-(2-amino-6-formylpyrimidin-4-yl) pyrrolidin-3-yl(methyl)carbamate The title compound was obtained following a similar procedure to that described in reference example 8a but using reference example 7b as starting material.

LC-MS (Method 2): $t_R$=1.78 min (broad peak); m/z 322 (MH$^+$).

Reference Example 9 tert-Butyl 1-(2-amino-6-(chloromethyl)pyrimidin-4-yl)azetidin-3-yl(methyl)carbamate Thionyl chloride (508 mg, 4.2 mmol) was added to a solution of the compound obtained in reference example 7a (1.2 g, 3.8 mmol) in THF (12 mL) and the resulting mixture was stirred under argon atmosphere for 1.5 h. The mixture is cooled to 0° C. and diisopropylethylamine (1.35 mL, 97.75 mmol) was added. The solvent was evaporated keeping the water bath temperature below 30° C. to give a crude material that was used as such in the following steps.

LC-MS (Method 2): $t_R$=1.86 min; m/z 328 (MH$^+$).

Example 1a 4-((Benzylamino)methyl)-6-(3-(methylamino) azetidin-1-yl) pyrimidin-2-amine A mixture of the compound obtained in reference example 8a (100 mg, 0.32 mmol), benzylamine (35 mg, 0.32 mmol), sodium triacetoxyborohydride (103.4 mg, 0.49 mmol) and acetic acid (28 µL, 0.49 mmol) in dichloromethane (6 ml) was stirred at room temperature overnight. The reaction mixture was evaporated to dryness and the residue was purified by chromatography over silica gel using mixtures of chloroform/ MeOH of increasing polarity as eluent, providing the Boc-protected precursor with quantitative yield. HCl (4 M solution in 1,4-dioxane, 5 mL) and MeOH (4 mL) were added to this intermediate and the mixture was stirred at room temperature for 2 hours and then it was evaporated to dryness. The residue was dissolved in MeOH (2 mL) and loaded on a sulfonic resin cartridge (Bond elut SCX-Varian, previously washed with MeOH). The cartridge was eluted with MeOH, that was discarded. It was then eluted with 2 N $NH_3$ solution in MeOH, that was collected and evaporated to dryness providing 65.7 mg of the title compound (yield: 67%).

LC-MS (Method 2): $t_R$=1.21 min; m/z 299 (MH$^+$).

Examples 1b-1t

The following compounds were obtained following a similar procedure to that described in example 1a, but using the corresponding starting materials in each case:

| Example | Name | Starting materials | Method (LC-MS) | $t_R$ (min) | m/z (MH$^+$) |
|---|---|---|---|---|---|
| 1b | 4-((Cyclopropylmethylamino)methyl)-6-(3-(methylamino)azetidin-1-yl)pyrimidin-2-amine | Ref Ex 8a and cyclopropylmethylamine | 2 | 0.85 | 263 |
| 1c | 4-((4-Fluorophenylamino)methyl)-6-(3-(methylamino)azetidin-1-yl)pyrimidin-2-amine | Ref Ex 8a and 4-fluoroaniline | 2 | 1.36 | 303 |
| 1d | Ethyl 4-(((2-amino-6-(3-(methylamino)azetidin-1-yl)pyrimidin-4-yl)methyl)amino)benzoate | Ref Ex 8a and ethyl 4-aminobenzoate (1) | 2 | 1.47 | 357 |
| 1e | Methyl 3-(3-(((2-amino-6-(3-(methylamino)azetidin-1-yl)pyrimidin-4-yl)methyl)amino)phenyl)propanoate | Ref Ex 8a and methyl 3-(3-aminophenyl)propanoate | 2 | 1.46 | 371 |
| 1f | Ethyl 2-(4-(((2-amino-6-(3-(methylamino)azetidin-1-yl)pyrimidin-4-yl)methyl)amino)phenyl)acetate | Ref Ex 8a and ethyl 2-(4-aminophenyl)acetate (1) | 2 | 1.54 | 371 |
| 1g | 4-(3-(Methylamino)azetidin-1-yl)-6-((pyrazin-2-ylamino)methyl)pyrimidin-2-amine | Ref Ex 8a and pyrazin-2-amine (2) (3) | 2 | 0.82 | 287 |
| 1h | 4-((Cyclopentylamino)methyl)-6-((3R)-3-(methylamino)pyrrolidin-1-yl)pyrimidin-2-amine | Ref Ex 8b and cyclopentylamine | 2 | 1.01 | 291 |
| 1i | 4-((Benzylamino)methyl)-6-((3R)-3-(methylamino)pyrrolidin-1-yl)pyrimidin-2-amine | Ref Ex 8b and benzylamine | 2 | 1.23 | 313 |
| 1j | 4-((3R)-3-(Methylamino)pyrrolidin-1-yl)-6-((phenethylamino)methyl)pyrimidin-2-amine | Ref Ex 8b and phenetylamine (3) | 2 | 1.34 | 327 |
| 1k | 4-((2,3-Dihydro-1H-inden-2-ylamino)methyl)-6-(3-(methylamino)azetidin-1-yl)pyrimidin-2-amine | Ref Ex 8a and 2-aminoindan | 2 | 1.43 | 325 |

| Example | Name | Starting materials | Method (LC-MS) | $t_R$ (min) | m/z (MH⁺) |
|---|---|---|---|---|---|
| 1l | 4-((Cyclohexylamino)methyl)-6-(3-(methylamino)azetidin-1-yl)pyrimidin-2-amine | Ref Ex 8a and cyclohexylamine | 2 | 1.19 | 291 |
| 1m | 4-(((((1R,2S,5R)-6,6-Dimethylbicyclo[3.1.1]heptan-2-yl)methyl)amino)methyl)-6-(3-(methylamino)azetidin-1-yl)pyrimidin-2-amine | Ref Ex 8a and (−)-cis-myrtanylamine | 2 | 1.72 | 345 |
| 1n | 4-((2-Cyclopentylethylamino)methyl)-6-(3-(methylamino)azetidin-1-yl)pyrimidin-2-amine | Ref Ex 8a and 2-cyclopentylethylamine | 2 | 1.45 | 305 |
| 1o | (S)-4-((2,3-Dihydro-1H-inden-1-ylamino)methyl)-6-(3-(methylamino)azetidin-1-yl)pyrimidin-2-amine | Ref Ex 8a and (S)-1-aminoindan | 2 | 1.43 | 325 |
| 1p | 4-((2-Adamantylamino)methyl)-6-(3-(methylamino)azetidin-1-yl)pyrimidin-2-amine | Ref Ex 8a and 2-adamantylamine hydrochloride | 2 | 1.64 | 343 |
| 1q | 4-(((2,2-Diethylcyclopropyl)methylamino)methyl)-6-(3-(methylamino)azetidin-1-yl)pyrimidin-2-amine | Ref Ex 8a and (2,2-diethylcyclopropyl)methylamine (3) | 2 | 1.53 | 319 |
| 1r | (R)-4-((2,3-Dihydro-1H-inden-1-ylamino)methyl)-6-(3-(methylamino)azetidin-1-yl)pyrimidin-2-amine | Ref Ex 8a and (R)-1-aminoindan (3) | 2 | 1.45 | 325 |
| 1s | Ethyl 3-(((2-amino-6-(3-(methylamino)azetidin-1-yl)pyrimidin-4-yl)methyl)amino)benzoate | Ref Ex 8a and ethyl 3-aminobenzoate (1) | 2 | 1.52 | 357 |
| 1t | 4-((Cyclopentylamino)methyl)-6-(3-(methylamino)azetidin-1-yl)pyrimidin-2-amine | Ref Ex 8a and cyclopentylamine | 2 | 1.00 | 277 |

(1) EtOH was used instead of MeOH in the Boc-deprotection step.
(2) 1,2-Dichloroethane was used instead of dichloromethane in the reductive amination step.
(3) Final product was purified by preparative HPLC Example 1t (Alternative Method)

4-((Cyclopentylamino)methyl)-6-(3-(methylamino)azetidin-1-yl)pyrimidin-2-amine (a) 2-Amino-N-cyclopentyl-6-hydroxypyrimidine-4-carboxamide Diisopropylethylamine (1.1 mL) and O-Benzotriazole-N,N,N'N'-tetramethyl-uronium-hexafluoro-phosphate (611 mg, 1.6 mmol) were added to a solution of 2-amino-6-hydroxy-pyrimidine-4-carboxylic acid (250 mg, 1.6 mmol) and cyclopenthylamine (137 mg, 1.6 mmol) in DMF (17 The resulting mixture was stirred at room temperature overnight. The solvent was evaporated and the residue was purified by chromatography over silica gel using mixtures of ethyl acetate/MeOH of increasing polarity as eluent, providing 100 mg of the desired compound (yield: 28%)

LC-MS (Method 2): $t_R$=1.02 min; m/z 223 (MH⁺).

(b) tert-Butyl 1-(2-amino-6-(cyclopentylcarbamoyl)pyrimidin-4-yl)azetidin-3-yl(methyl)carbamate A mixture of the compound obtained in section (a) (102 mg, 0.46 mmol), the compound obtained in reference example 2 (222 mg, 0.59 mmol, 50%), triethylamine (2.7 mL), (Benzotriazol-1-yloxy)tripyrrolidinophosphonium hexafluorophosphate (382.1 g, 0.73 mmol) in acetonitrile (4.5 mL) was heated in a pressure tube at 80° C. for 24 h. The solvent was evaporated and the residue was dissolved in water, pH adjusted to pH=8-9 and extracted three times with chloroform. The combined organic phases were dried over Na₂SO₄, concentrated to dryness, and the residue was purified by chromatography over silica gel using mixtures of hexane/ethyl acetate of increasing polarity as eluent, providing 73 mg of the desired compound (yield: 41%)

LC-MS (Method 2): LR=2.04 min; m/z 391 (MH⁺).

(c) Title Compound

A 1M solution of borane in THF (0.94 mL) was added to a solution of compound prepared in section (b) (73 mg, 0.19 mmol) in THF (0.78 mL) cooled to 0° C. and previously purged under argon atmosphere. The resulting mixture was stirred at room temperature overnight. Additional 1M Borane in THF solution (0.94 mL) was added and the resulting mixture was stirred at room temperature for 4 hours. A mixture 1:1 of acetic acid: MeOH (0.8 mL) was added and the resulting mixture was stirred overnight. Solvents were eliminated under vacuum to give the BOC-precursor. 4N aqueous HCl was added and the resulting solution was stirred at room temperature for 2 h and then it was evaporated to dryness. The residue was diluted with water, pH adjusted to pH=1-2 and extracted twice with chloroform. 2N NaOH was added to the aqueous phase until pH=8-9 and extracted three times with chloroform. The combined organic phases were dried over Na₂SO₄, concentrated to dryness and the residue purified by preparative HPLC providing 2.95 mg of the title compound (5% yield).

LC-MS (Method 2): $t_R$=0.99 min; m/z 277 (MH⁺).

Example 2a

4-(3-(Methylamino)azetidin-1-yl)-6-((pentylamino)methyl)pyrimidin-2-amine

A mixture of the compound obtained in reference example 8a (70 mg, 0.23 mmol), pentylamine (20 mg, 0.23 mmol), sodium triacetoxyborohydride (72.4 mg, 0.34 mmol) and acetic acid (20 µL, 0.34 mmol) in dichloromethane (5 mL) was stirred at room temperature overnight. The reaction mixture was evaporated to dryness, providing the Boc-protected precursor as a crude product. A 2:1 v/v mixture of dichloromethane and trifluoroacetic acid (2 mL) was added to this intermediate and the mixture was stirred at room temperature for 2 hours and then it was evaporated to dryness. The residue was dissolved in MeOH (2 mL) and loaded on a sulfonic resin cartridge (Bond elut SCX-Varian, previously washed with MeOH). The cartridge was eluted with MeOH, that was discarded. It was then eluted with 2 N $NH_3$ solution in MeOH, that was collected and evaporated to dryness providing 46.1 mg of the title compound (yield: 72%).

LC-MS (Method 2): $t_R$=1.25 min; m/z 279 (MH$^+$).

Examples 2b-2 am

The following compounds were obtained following a similar procedure to that described in example 2a, but using the corresponding starting materials in each case:

| Example | Name | Starting materials | Method (LC-MS) | $t_R$ (min) | m/z (MH$^+$) |
|---|---|---|---|---|---|
| 2b | 4-(3-(Methylamino)azetidin-1-yl)-6-((3-phenylpropylamino)methyl)pyrimidin-2-amine | Ref Ex 8a and 3-phenylpropylamine | 2 | 1.43 | 327 |
| 2c | 4-(3-(Methylamino)azetidin-1-yl)-6-((4-phenylbutylamino)methyl)pyrimidin-2-amine | Ref Ex 8a and 4-phenylbutylamine | 2 | 1.56 | 341 |
| 2d | 4-((Cyclohexylmethylamino)methyl)-6-(3-(methylamino)azetidin-1-yl)pyrimidin-2-amine | Ref Ex 8a and cyclohexylmethylamine | 2 | 1.41 | 305 |
| 2e | 4-(3-(Methylamino)azetidin-1-yl)-6-((phenethylamino)methyl)pyrimidin-2-amine | Ref Ex 8a and phenethylamine | 2 | 1.32 | 313 |
| 2f | 4-(3-(Methylamino)azetidin-1-yl)-6-((2-(pyridin-3-yl)ethylamino)methyl)pyrimidin-2-amine | Ref Ex 8a and 3-(2-aminoethyl)pyridine (1) | 2 | 0.92 | 314 |
| 2g | 4-(3-(Methylamino)azetidin-1-yl)-6-(((1-phenylcyclopropyl)methylamino)methyl)pyrimidin-2-amine | Ref Ex 8a and (1-phenylcyclopropyl)methylamine | 2 | 1.49 | 339 |
| 2h | 4-((Cycloheptylamino)methyl)-6-(3-(methylamino)azetidin-1-yl)pyrimidin-2-amine | Ref Ex 8a and cycloheptylamine | 2 | 1.34 | 305 |
| 2i | 4-((4-Chlorobenzylamino)methyl)-6-(3-(methylamino)azetidin-1-yl)pyrimidin-2-amine | Ref Ex 8a and 4-chlorobenzylamine | 2 | 1.49 | 333/335 |
| 2j | 4-(3-(Methylamino)azetidin-1-yl)-6-(((1R)-1-phenylethylamino)methyl)pyrimidin-2-amine | Ref Ex 8a and (R)-1-phenylethylamine | 2 | 1.41 | 313 |
| 2k | 4-(3-(Methylamino)azetidin-1-yl)-6-(((1S)-1-phenylethylamino)methyl)pyrimidin-2-amine | Ref Ex 8a and (S)-1-phenylethylamine | 2 | 1.41 | 313 |
| 2l | 4-(3-(Methylamino)azetidin-1-yl)-6-((naphthalen-1-ylmethylamino)methyl)pyrimidin-2-amine | Ref Ex 8a and 1-naphthalenemethylamine | 2 | 1.53 | 349 |
| 2m | 4-(2-(((2-Amino-6-(3-(methylamino)azetidin-1-yl)pyrimidin-4-yl)methyl)amino)ethyl)benzonitrile | Ref Ex 8a and 4-(2-aminoethyl)benzonitrile (1) | 2 | 1.24 | 338 |
| 2n | 4-((2,3-Dihydro-1H-inden-5-ylamino)methyl)-6-(3-(methylamino)azetidin-1-yl)pyrimidin-2-amine | Ref Ex 8a and 5-aminoindan (1) | 2 | 1.69 | 325 |
| 2o | 4-((4-(1H-Pyrazol-1-yl)phenylamino)methyl)-6-(3-(methylamino)azetidin-1-yl)pyrimidin-2-amine | Ref Ex 8a and 4-(1H-pyrazol-1-yl)aniline (1) | 2 | 1.33 | 351 |
| 2p | 4-(((2-Amino-6-(3-(methylamino)azetidin-1-yl)pyrimidin-4-yl)methyl)amino)benzonitrile | Ref Ex 8a and 4-aminobenzonitrile (1) | 2 | 1.26 | 310 |
| 2q | 4-(3-(Methylamino)azetidin-1-yl)-6-((3-(2-methylthiazol-4-yl)phenylamino)methyl)pyrimidin-2-amine | Ref Ex 8a and 3-(2-methylthiazol-4-yl)aniline (1) | 2 | 1.54 | 382 |
| 2r | 3-(((2-Amino-6-(3-(methylamino)azetidin-1-yl)pyrimidin-4-yl)methyl)amino)benzonitrile | Ref Ex 8a and 3-aminobenzonitrile (1) | 2 | 1.34 | 310 |
| 2s | 4-((((2-Amino-6-(3-(methylamino)azetidin-1-yl)pyrimidin-4-yl)methyl)amino)methyl)benzonitrile | Ref Ex 8a and 4-(aminomethyl)benzonitrile | 2 | 1.20 | 324 |

-continued

| Example | Name | Starting materials | Method (LC-MS) | $t_R$ (min) | m/z (MH$^+$) |
|---------|------|--------------------|----------------|-------------|--------------|
| 2t | 4-((2,3-Dihydro-1H-inden-4-ylamino)methyl)-6-(3-(methylamino)azetidin-1-yl)pyrimidin-2-amine | Ref Ex 8a and 4-aminoindan (1) | 2 | 1.68 | 325 |
| 2u | Methyl 3-((((2-amino-6-(3-(methylamino)azetidin-1-yl)pyrimidin-4-yl)methyl)amino)methyl)benzoate | Ref Ex 8a and methyl 3-(aminomethyl)benzoate | 2 | 1.29 | 357 |
| 2v | 4-(3-(Methylamino)azetidin-1-yl)-6-((4-methylbenzylamino)methyl)pyrimidin-2-amine | Ref Ex 8a and 4-methylbenzylamine (1) | 2 | 1.38 | 313 |
| 2w | 4-((2-Chlorophenethylamino)methyl)-6-(3-(methylamino)azetidin-1-yl)pyrimidin-2-amine | Ref Ex 8a and 2-(2-chlorophenyl)ethylamine | 2 | 1.48 | 347/349 |
| 2x | 4-((3-Chlorophenethylamino)methyl)-6-(3-(methylamino)azetidin-1-yl)pyrimidin-2-amine | Ref Ex 8a and 2-(3-chlorophenyl)ethylamine | 2 | 1.54 | 347/349 |
| 2y | 4-((Benzhydrylamino)methyl)-6-(3-(methylamino)azetidin-1-yl)pyrimidin-2-amine | Ref Ex 8a and benzhydrylamine | 2 | 1.81 | 375 |
| 2z | 2-(((2-Amino-6-(3-(methylamino)azetidin-1-yl)pyrimidin-4-yl)methyl)amino)benzonitrile | Ref Ex 8a and 2-aminobenzonitrile (1) | 2 | 1.40 | 310 |
| 2aa | 2-(((2-Amino-6-(3-(methylamino)azetidin-1-yl)pyrimidin-4-yl)methyl)amino)-1-phenylethanol | Ref Ex 8a and 2-amino-1-phenylethanol (1) | 2 | 1.12 | 329 |
| 2ab | (2R)-2-(((2-Amino-6-(3-(methylamino)azetidin-1-yl)pyrimidin-4-yl)methyl)amino)-3-phenylpropan-1-ol | Ref Ex 8a and (R)-2-amino-3-phenylpropan-1-ol (1) | 2 | 1.22 | 343 |
| 2ac | Ethyl 2-(((2-amino-6-(3-(methylamino)azetidin-1-yl)pyrimidin-4-yl)methyl)amino)benzoate | Ref Ex 8a and ethyl 2-aminobenzoate (1) | 2 | 1.78 | 357 |
| 2ad | 4-((2-Ethylphenylamino)methyl)-6-(3-(methylamino)azetidin-1-yl)pyrimidin-2-amine | Ref Ex 8a and 2-ethylaniline | 2 | 1.68 | 313 |
| 2ae | 4-((2-Fluorophenethylamino)methyl)-6-(3-(methylamino)azetidin-1-yl)pyrimidin-2-amine | Ref Ex 8a and 2-(2-fluorophenyl)ethylamine (1) | 2 | 1.36 | 331 |
| 2af | 4-((1,2-Diphenylethylamino)methyl)-6-(3-(methylamino)azetidin-1-yl)pyrimidin-2-amine | Ref Ex 8a and 1,2-diphenylethylamine | 2 | 1.87 | 389 |
| 2ag | 4-((4-Chlorophenethylamino)methyl)-6-(3-(methylamino)azetidin-1-yl)pyrimidin-2-amine | Ref Ex 8a and 2-(4-chlorophenyl)ethylamine (1) | 2 | 1.57 | 347/349 |
| 2ah | 4-((2,2-Diphenylethylamino)methyl)-6-(3-(methylamino)azetidin-1-yl)pyrimidin-2-amine | Ref Ex 8a and 2,2-diphenylethylamine (1) | 2 | 1.78 | 389 |
| 2ai | 4-(3-(Methylamino)azetidin-1-yl)-6-(((2R)-2-phenylpropylamino)methyl)pyrimidin-2-amine | Ref Ex 8a and (R)-2-phenyl-1-propylamine (1) | 2 | 1.49 | 327 |
| 2aj | 4-(3-(Methylamino)azetidin-1-yl)-6-(((2S)-2-phenylpropylamino)methyl)pyrimidin-2-amine | Ref Ex 8a and (S)-2-phenyl-1-propylamine (1) | 2 | 1.43 | 327 |
| 2ak | 4-((3-Fluorophenethylamino)methyl)-6-(3-(methylamino)azetidin-1-yl)pyrimidin-2-amine | Ref Ex 8a and 2-(3-fluorophenyl)ethylamine (1) | 2 | 1.38 | 331 |
| 2al | 4-((4-Fluorophenethylamino)methyl)-6-(3-(methylamino)azetidin-1-yl)pyrimidin-2-amine | Ref Ex 8a and 2-(4-fluorophenyl)ethylamine (1) | 2 | 1.38 | 331 |
| 2am | 4-((Methyl(phenethyl)amino)methyl)-6-(3-(methylamino)azetidin-1-yl)pyrimidin-2-amine | Ref Ex 8a and N-methylphenethylamine (1) | 2 | 1.55 | 327 |

(1) Final product was purified by preparative HPLC

Example 3a 4-(3-(Methylamino)azetidin-1-yl)-6-((pyridin-3-ylamino)methyl)pyrimidin 2-amine 3-Aminopyridine (11.3 mg, 0.12 mmol) and dibutyltin dichloride (3.7 mg, 0.012 mmol) were added to a solution of the compound obtained in reference example 8a (37 mg, 0.12 mmol) in THF (1.5 ml) and the mixture was stirred at room temperature for 5 min. Phenylsilane (26.1 mg, 0.24 mmol) was then added and the reaction mixture was stirred at room temperature overnight. It was evaporated to dryness and the residue was purified by chromatography over silica gel using mixtures of EtOAc/MeOH of increasing polarity as eluent, providing 17 mg of the Boc-protected precursor (yield: 36%).

HCl (4 M solution in 1,4-dioxane, 2 ml) and MeOH (4 mL) were added to this intermediate and the mixture was stirred at room temperature for 2 hours and then it was evaporated to dryness. The residue was dissolved in MeOH (2 mL) and loaded on a sulfonic resin cartridge (Bond elut SCX-Varian, previously washed with MeOH). The cartridge was eluted with MeOH, that was discarded. It was then eluted with 2 N $NH_3$ solution in MeOH, that was collected and evaporated to dryness providing 9.5 mg of the title compound (yield: 76%).
LC-MS (Method 2): $t_R$=0.95 min; m/z 286 (MH$^+$).

Example 3b 4-(3-(Methylamino)azetidin-1-yl)-6-((pyridin-2-ylamino)methyl)pyrimidin-2-amine The title compound was obtained following a similar procedure to that described in example 3a but using reference example 8a and 2-aminopyridine as starting materials.
LC-MS (Method 2): $t_R$=1.08 min; m/z 286 (MH$^+$).

Example 4a 3-(3-4(2-Amino-6-(3-(methylamino)azetidin-1-yl)pyrimidin-4-yl)methyl)amino)ohenyl)propan-1-ol Lithium aluminum hydride (0.27 mL of a 1 N solution in THF, 0.27 mmol) was slowly added under argon to a solution of example 1e (25 mg, 0.07 mmol) in THF (1 mL) cooled at 0° C. The ice bath was removed and it was allowed to warm, stifling at room temperature overnight. It was then diluted with 1 M sodium tartrate solution and chloroform, phases were separated and the aqueous phase was extracted with chloroform. The combined organic phases were dried over anhydrous $Na_2SO_4$ and concentrated to dryness, providing 17.8 mg of the title compound (yield: 77%).
LC-MS (Method 2): $t_R$=1.23 min; m/z 343 (MH$^+$).

Examples 4b-4-c

The following compounds were obtained following a similar procedure to that described in example 4a, but using the corresponding starting material in each case:

| Example | Name | Starting materials | Method (LC-MS) | $t_R$ (min) | m/z (MH$^+$) |
|---|---|---|---|---|---|
| 4b | 2-(4-(((2-Amino-6-(3-(methylamino)azetidin-1-yl)pyrimidin-4-yl)methyl)amino)phenyl)ethanol | Ex 1f | 2 | 1.06 | 329 |
| 4c | (4-(((2-Amino-6-(3-(methylamino)azetidin-1-yl)pyrimidin-4-yl)methyl)amino)phenyl)methanol | Ex 1d | 2 | 0.95 | 315 |

Example 5

4-((Cyclopentyl(methyl)amino)methyl)-6-(3-(methylamino)azetidin-1-yl)pyrimidin-2-amine (a) tert-Butyl 1-(2-amino-6-((cyclopentylamino)methyl)pyrimidin-4-yl)azetidin-3-yl(methyl)carbamate A mixture of the compound obtained in reference example 8a (200 mg, 0.65 mmol), cyclopentylamine (55.4 mg, 0.65 mmol), sodium triacetoxyborohydride (206.9 mg, 0.98 mmol) and acetic acid (56 µL, 0.98 mmol) in dichloromethane (6 ml) was stirred at room temperature overnight. The reaction mixture was evaporated to dryness and the residue was purified by chromatography over silica gel using mixtures of chloroform/MeOH of increasing polarity as eluent, providing 217 mg of the desired compound (yield: 88%).
LC-MS (Method 2): $t_R$=1.74 min; m/z 377 (MH$^-$).

(b) Title Compound

A mixture of the compound obtained in section (a) (110 mg, 0.29 mmol), paraformaldehyde (17.5 mg, 0.58 mmol), sodium triacetoxyborohydride (185.8 mg, 0.88 mmol) and acetic acid (50 µL, 0.88 mmol) in dichloromethane (7.3 mL) was stirred at room temperature overnight. The reaction mixture was evaporated to dryness, providing the Boc-protected precursor impurified with starting material. HCl (4 M solution in 1,4-dioxane, 5 mL) and MeOH (4 mL) were added to this intermediate and the mixture was stirred at room temperature for 2 hours and then it was evaporated to dryness. The crude product thus obtained was purified by preparative HPLC and the fractions containing the product were evaporated to dryness, providing 3.1 mg of the title compound (yield: 4%).
LC-MS (Method 2): $t_R$=1.25 min; m/z 291 (MH$^+$).

Example 6a 4-((Isobutylamino)methyl)-6-(3-(methylamino)azetidin-1-yl)pyrimidin-2-amine A mixture of the compound obtained in reference example 9 (70 mg, 0.21 mmol) isobutylamine (156 mg, 2.1 mmol) in acetonitrile (2 mL) was heated at 75° C. overnight. The reaction mixture was evaporated to dryness and diluted with chloroform and water. The phases were separated and the aqueous phase was extracted twice again with chloroform. The combined organic phases were dried over $MgSO_4$ and concentrated to dryness, thus obtaining 78 mg of the Boc-protected precursor. A 2:1 v/v mixture of dichloromethane and trifluoroacetic acid (1.5 mL) was added to this intermediate and the mixture was stirred at room temperature for 1 hour and then it was evaporated to dryness. The residue was diluted with chloroform and water. The phases were separated and the aqueous phase was extracted twice again with chloroform. 2N NaOH was added to the aqueous phase until pH=8-9 and extracted twice again with chloroform. The combined organic phases were dried over $MgSO_4$, concentrated to dryness and the residue purified by preparative HPLC providing 11 mg of the title compound (20% yield).
LC-MS (Method 2): $t_R$=1.11 min; m/z 265 (MM.

Examples 6b

4-((Cyclopentylmethylamino)methyl)-6-(3-(methylamino)azetidin-1-yl)pyrimidin-2-amine A mixture of the compound obtained in reference example 9 (100 mg, 0.30 mmol) cyclopentylmethylamine (303 mg, 3 mmol) in acetonitrile (2 mL) was heated at 75° C. in a pressure tube overnight. The reaction mixture was evaporated to dryness and diluted with chloroform and water. The phases were separated and the aqueous phase was extracted twice again with chloroform. The combined organic phases were dried over $MgSO_4$, concentrated to dryness, and the residue was purified by chromatography over silica gel using mixtures of chloroform/MeOH of increasing polarity as eluent, providing 50 mg of Boc-protected precursor (yield: 42%). HCl (4 M solution in 1,4-dioxane, 5 mL) and MeOH (4 mL) were added to this intermediate and the mixture was stirred at room temperature for 1 hour and then it was evaporated to dryness. The residue was dissolved in Meal (2 mL) and loaded on a sulfonic resin cartridge (Bond elut SCX-Varian, previously washed with MeOH). The cartridge was eluted with MeOH, that was discarded. It was then eluted with 2 N $NH_3$ solution in Meal, that was collected and evaporated to dryness providing 34 mg of the title compound (yield: 83%).

LC-MS (Method 2): $t_R$=1.32 min; m/z 291 ($MH^+$).

Examples 6c-6j

The following compounds were obtained following a similar procedure to that described in example 6a, but using the corresponding starting material in each case:

Example 7

Competitive Binding Assay for [$^3$H]-Histamine to the Human Histamine $H_4$ Receptor Membrane extracts were used to perform the test that were prepared from a stable recombinant CHO cell line expressing the human histamine $H_4$ receptor (Euroscreen/Perkin-Elmer).

The compounds to be tested were incubated at the desired concentration in duplicate with 10 nM [$^3$H]-histamine and 15 μg of membrane extract in a total volume of 250 μL of 50 mM Tris-HCl, pH 7.4, 1.25 mM EDTA for 60 minutes at 25° C. Non-specific binding was defined in the presence of 100 μM of unlabelled histamine. The reaction was interrupted by filtration by means of a vacuum manifold (Multiscreen Millipore) in 96 well plates (MultiScreen HIS Millipore) that were previously treated with 0.5% polyethylenimine for 2 hours at 0° C. The plates were subsequently washed with 50 mM Tris (pH 7.4), 1.25 mM EDTA at 0° C., and the filters were dried for 1 hour at 50-60° C. before adding the scintillation liquid in order to determine bound radioactivity by means of a beta scintillation counter.

All the compounds described in the examples were assayed in this test and exhibited more than 50% inhibition of binding to human histamine receptor $H_4$ at a 1 μM concentration.

Example 8

Histamine-Induced Shape Change Assay (Gated Autofluorescence Forward Scatter Assay, GAFS) in Human Eosinophils In this assay the shape change induced by histamine in human eosinophils is determined by flow cytometry, detected as an increase in the size of the cells (forward scatter, FSC).

| Example | Name | Starting materials | Method (LC-MS) | $t_R$ (min) | m/z ($MH^+$) |
|---|---|---|---|---|---|
| 6c | 4-((Cyclopropylamino)methyl)-6-(3-(methylamino)azetidin-1-yl)pyrimidin-2-amine | Ref Ex 9 and cyclopropylamine | 2 | 0.89 | 249 |
| 6d | 4-((tert-Butylamino)methyl)-6-(3-(methylamino)azetidin-1-yl)pyrimidin-2-amine | Ref Ex 9 and tert-butylamine (1) | 2 | 0.92 | 265 |
| 6e | 4-((Isopropylamino)methyl)-6-(3-(methylamino)azetidin-1-yl)pyrimidin-2-amine | Ref Ex 9 and isopropylamine | 2 | 0.72 | 251 |
| 6f | 4-((4,4-Difluorocyclohexylamino)methyl)-6-(3-(methylamino)azetidin-1-yl)pyrimidin-2-amine | Ref Ex 9 and 4,4-difluorocyclohexylamine | 2 | 1.27 | 327 |
| 6g | 4-(3-(methylamino)azetidin-1-yl)-6-((2,2,2-trifluoroethylamino)methyl)pyrimidin-2-amine | Ref Ex 9 and 2,2,2-trifluoroethylamine | 2 | 1.07 | 290 |
| 6h | 4-(((1R,2R,4S)-bicyclo[2.2.1]heptan-2-ylamino)methyl)-6-(3-(methylamino)azetidin-1-yl)pyrimidin-2-amine | Ref Ex 9 and -(1R,2R,4S)-bicyclo[2.2.1]heptan-2-ylamine | 2 | 1.26 | 302 |
| 6i | (S)-4-((sec-butylamino)methyl)-6-(3-(methylamino)azetidin-1-yl)pyrimidin-2-amine | Ref Ex 9 and (S)-sec-butylamine | 2 | 1.07 | 264 |
| 6j | (R)-4-((sec-butylamino)methyl)-6-(3-(methylamino)azetidin-1-yl)pyrimidin-2-amine | Ref Ex 9 and (R)-sec-butylamine | 2 | 1.07 | 264 |

(1) Ref Ex 9 and tert-butylamine were heated for 3 days instead of overnight.

Polymorphonuclear leucocytes (PMNL, fraction containing neutrophils and eosinophils) were prepared from whole blood of human healthy volunteers. Briefly, erythrocytes were separated by sedimentation in 1.2% Dextran (SIGMA), and the leucocyte-rich fraction (PMNL) was isolated from the top layer by centrifugation at 450 g for 20 min in the presence of Ficoll-Paque® (Biochrom). PMNLs were resuspended in PBS buffer at a concentration of $1.1 \times 10^6$ cells/ml/tube and were pretreated with different concentrations of test compounds (dissolved in PBS) for 30 min at 37° C. and then stimulated with 300 nM histamine (Fluke) for 5 min. Finally, paraformaldehyde (1% final concentration in PBS) was added to terminate the reaction and maintain cell shape. Cell shape change was analyzed by flow cytometry (FACS Calibur, BD Biosystems). Eosinophils in PMNL were gated based on their higher autofluorescence relative to that of neutrophils (fluorescence channel FL2). Cell shape change was monitored in forward scatter signals (FSC). Results are expressed as percentage inhibition of shape change induced by histamine for each concentration of test compound.

All the compounds described in the examples except examples 1h, 1i, 1j, 4a, 4b, 4c and 6a to 6j were assayed in this test and produced more than 50% inhibition of histamine-induced human eosinophil shape change at 1 μM.

Example 9 hERG Assay

The inhibition of the hERG channel was determined by an automated modification of the conventional patch clamp method. The compounds to be tested were assayed at the desired concentration(s) and the result was expressed as % inhibition.

Several compounds of the invention were tested in this assay and gave less than 50% inhibition at 10 pNl.

Example 10

Murine Atopic Dermatitis Model by Multiple Oxazolone Challenges

Method: Male BALB/c mice (n=5-7 per group) were sensitised on Day 1 by the topical application of 50 μL of 1% oxazolone in acetone/olive oil (4:1) on the abdominal skin. On days 8, 10, 12, 15, 17, 19, 22, 24 and 26, animals received repeated challenges with 25 μL of 0.2% oxazolone, applied topically on the inner side of their right ear. On days 8-26, 25 μL of a solution of the test compound (prepared by dissolving compound in acetone/olive oil 4:1 and heating) at the desired concentration were administered on the outer side of the right ears. On days 12, 19 and 26, right ear thickness was determined with a calliper one hour after oxazolone application.

The compounds of examples 1b and 1t were tested in this assay and gave >70% inhibition of oxazolone-induced ear inflammation at day 26 when administered at a concentration of 0.5%.

The invention claimed is:
1. A compound of formula I or a salt thereof

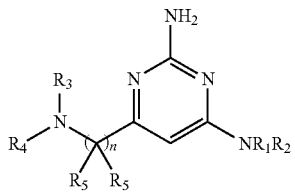

I wherein:
$R_1$ and $R_2$ form, together with the N atom to which they are bound, a saturated heterocyclic group which contains 1 N atom and does not contain any other heteroatom, wherein the heterocyclic group is substituted with one —$NR_aR_b$ group and is optionally substituted with one or more $C_{1-4}$ alkyl groups;
wherein the heterocyclic group is a 4- to 7-membered monocyclic group,
$R_a$ represents H or $C_{1-4}$ alkyl;
$R_b$ represents H or $C_{1-4}$ alkyl; or
$R_a$ and $R_b$ form, together with the N atom to which they are bound, an azetidinyl, pyrrolidinyl, piperidinyl, or azepanyl group that is optionally substituted with one or more $C_{1-4}$ alkyl groups;
$R_3$ represents H or $C_{1-8}$ alkyl;
$R_4$ represents $C_{1-8}$ alkyl optionally substituted with one or more halogen, $C_{3-10}$ cycloalkyl-$C_{0-4}$ alkyl, heterocycloalkyl-$C_{0-4}$ alkyl, aryl-$C_{0-4}$ alkyl, or heteroaryl-$C_{0-4}$ alkyl; wherein any $C_{0-4}$ alkyl in the $C_{3-10}$ cycloalkyl-$C_{0-4}$ alkyl, heterocycloalkyl-$C_{0-4}$ alkyl, aryl-$C_{0-4}$ alkyl and heteroaryl-$C_{0-4}$ alkyl groups is optionally substituted with one or more $R_6$ groups, any of the cycloalkyl and heterocycloalkyl groups are optionally substituted with one or more substituents independently selected from $C_{1-8}$ alkyl and halogen, and any of the aryl and heteroaryl groups are optionally substituted with one or more $R_7$ groups;
each $R_5$ independently represents H or $C_{1-8}$ alkyl;
each $R_6$ independently represents $C_{1-8}$ alkyl, halogen, hydroxy$C_{0-6}$ alkyl, $C_{3-10}$ cycloalkyl optionally substituted with one or more $C_{1-8}$ alkyl groups, or phenyl optionally substituted with one or more $R_8$; and optionally two $R_6$ groups on the same carbon atom are bonded together to form a —$C_{2-5}$ alkylene- group that is optionally substituted with one or more $C_{1-8}$ alkyl groups;
each $R_7$ independently represents $C_{1-8}$ alkyl, halo$C_{1-6}$ alkyl, halogen, $C_{1-6}$ alkoxy, halo$C_{1-6}$ alkoxy, —CN, $C_{1-6}$ alkylthio, $C_{2-4}$ alkynyl, hydroxy$C_{0-6}$ alkyl, $CO_2R_9$—$C_{0-6}$ alkyl, $C_{3-10}$ cycloalkyl, heterocycloalkyl, aryl or heteroaryl; wherein any of the cycloalkyl, heterocycloalkyl, aryl or heteroaryl groups in $R_7$ are optionally substituted with one or more $C_{1-8}$ alkyl groups;
each $R_8$ independently represents $C_{1-8}$ alkyl, halo$C_{1-6}$ alkyl, halogen, $C_{1-6}$ alkoxy, halo$C_{1-6}$ alkoxy or —CN,
each $R_9$ independently represents H or $C_{1-8}$ alkyl, and
n represents 1 or 2.
2. The compound of claim 1, wherein n is 1.
3. The compound of claim 1, wherein $R_5$ is H or methyl.
4. The compound of claim 1, wherein $R_3$ is H or methyl.
5. The compound of claim 1, wherein $R_4$ is selected from the group consisting of $C_{1-8}$ alkyl, $C_{3-10}$ cycloalkyl-$C_{0-4}$ alkyl, heterocycloalkyl-$C_{0-4}$ alkyl, aryl-$C_{0-4}$ alkyl and heteroaryl-$C_{0-4}$ alkyl, and wherein the $C_{0-4}$ alkyl is optionally substituted with one or more $R_6$ groups, wherein any of the cycloalkyl or heterocycloalkyl groups are optionally substituted with one or more substituents independently selected from $C_{1-8}$ alkyl and halogen, and wherein any of the aryl or heteroaryl groups are optionally substituted with one or more $R_7$ groups.
6. The compound of claim 1, wherein $R_4$ is selected from the group consisting of $C_{3-8}$ alkyl, and $C_{3-6}$ cycloalkyl-$C_{0-1}$ alkyl, and wherein the cycloalkyl is optionally substituted with one or more substituents independently selected from the group consisting of $C_{1-8}$ alkyl and halogen.
7. The compound of claim 1, wherein $R_4$ is selected from the group consisting of $C_{3-8}$ alkyl, and $C_{3-6}$ cycloalkyl-$C_{0-1}$ alkyl, wherein the alkyl is substituted with one or more $R_6$ groups and the cycloalkyl is substituted with one or more substituents independently selected from $C_{1-8}$ alkyl and halogen.

8. The compound of claim 1, wherein $R_4$ represents $C_{3-6}$ cycloalkyl-$C_1$ alkyl.

9. The compound of claim 1, wherein $R_4$ is selected from the group consisting of cyclopropylmethyl, cyclobutyl, and cyclopentyl.

10. The compound of claim 1, wherein $R_1$ and $R_2$ together form with the N atom to which they are bound, a saturated heterocyclic group having the formula selected from the group consisting of:

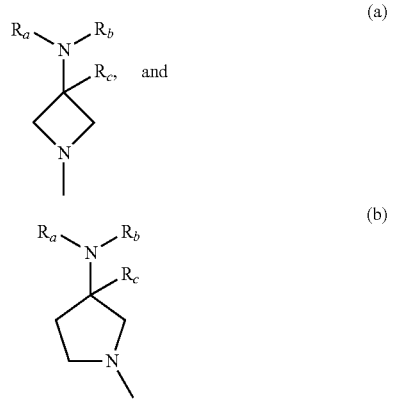

wherein $R_c$ represents H or $C_{1-4}$ alkyl.

11. The compound of claim 10, wherein $R_1$ and $R_2$ form, together with the N atom to which they are bound, a saturated heterocyclic group selected from the structures (a), and $R_c$ represents H.

12. The compound of claim 10, wherein $R_1$ and $R_2$ form, together with the N atom to which they are bound, the saturated heterocyclic group of formula (b), and $R_c$ represents H.

13. The compound of claim 10, wherein $R_c$ represents a methyl.

14. The compound of claim 10, wherein $R_a$ and $R_b$ are independently selected from the group consisting of H, methyl, and ethyl.

15. The compound of claim 11, wherein $R_a$ is H and $R_b$ is methyl.

16. The compound according to claim 1 selected from the group consisting of:
(a) 4-((Cyclopropylmethylamino)methyl)-6-(3-(methylamino)azetidin-1-yl)pyrimidin-2-amine, or a salt thereof;
(b) 4-((2-Adamantylamino)methyl)-6-(3-(methylamino)azetidin-1-yl)pyrimidin-2-amine, or a salt thereof;
(c) 4-(((2,2-Diethylcyclopropyl)methylamino)methyl)-6-(3-(methylamino)azetidin-1-yl)pyrimidin-2-amine, or a salt thereof;
(d) 4-((Cyclopentylamino)methyl)-6-(3-(methylamino)azetidin-1-yl)pyrimidin-2-amine, or a salt thereof;
(e) 4-(3-(Methylamino)azetidin-1-yl)-6-((pentylamino)methyl)pyrimidin-2-amine, or a salt thereof;
(f) 4-((Cyclopentyl(methyl)amino)methyl)-6-(3-(methylamino)azetidin-1-yl)pyrimidin-2-amine, or a salt thereof;
(g) 4-((isobutylamino)methyl)-6-(3-(methylamino)azetidin-1-yl)pyrimidin-2-amine, or a salt thereof;
(h) 4-((Cyclopropylamino)methyl)-6-(3-(methylamino)azetidin-1-yl)pyrimidin-2-amine, or a salt thereof;
(i) 4-((tert-Butylamino)methyl)-6-(3-(methylamino)azetidin-1-yl)pyrimidin-2-amine, or a salt thereof;
(j) 4-((Isopropylamino)methyl)-6-(3-(methylamino)azetidin-1-yl)pyrimidin-2-amine, or a salt thereof;
(k) 4-(3-(methylamino)azetidin-1-yl)-6-((2,2,2-trifluoroethylamino)methyl)pyrimidin-2-amine, or a salt thereof;
(l) 4-(((1R,2R,4S)-bicyclo[2.2.1]heptan-2-ylamino)methyl)-6-(3-(methylamino)azetidin-1-yl)pyrimidin-2-amine, or a salt thereof;
(m) (S)-4-((sec-butylamino)methyl)-6-(3-(methylamino)azetidin-1-yl)pyrimidin-2-amine, or a salt thereof; and
(n) (R)-4-((sec-butylamino)methyl)-6-(3-(methylamino)azetidin-1-yl)pyrimidin-2-amine, or a salt thereof.

17. A pharmaceutical composition comprising a compound of formula I or a salt thereof

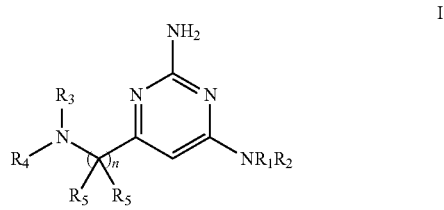

wherein:
$R_1$ and $R_2$ form, together with the N atom to which they are bound, a saturated heterocyclic group which contains 1N atom and does not contain any other heteroatom, wherein the heterocyclic group is substituted with one —$NR_aR_b$ group and is optionally substituted with one or more $C_{1-4}$ alkyl groups;
wherein the heterocyclic group is a 4- to 7-membered monocyclic group,
$R_a$ represents H or $C_{1-4}$ alkyl;
$R_b$ represents H or $C_{1-4}$ alkyl; or
$R_a$ and $R_b$ form, together with the N atom to which they are bound, an azetidinyl, pyrrolidinyl, piperidinyl or azepanyl group that is optionally substituted with one or more $C_{1-4}$ alkyl groups;
$R_3$ represents H or $C_{1-8}$ alkyl;
$R_4$ represents $C_{1-8}$ alkyl optionally substituted with one or more halogen, $C_{3-10}$ cycloalkyl-$C_{0-4}$ alkyl, heterocycloalkyl-$C_{0-4}$ alkyl, aryl-$C_{0-4}$ alkyl, or heteroaryl-$C_{0-4}$ alkyl; wherein any $C_{0-4}$ alkyl in the $C_{3-10}$ cycloalkyl-$C_{0-4}$ alkyl, heterocycloalkyl-$C_{0-4}$ alkyl, aryl-$C_{0-4}$ alkyl and heteroaryl-$C_{0-4}$ alkyl groups is optionally substituted with one or more $R_6$ groups, any of the cycloalkyl and heterocycloalkyl groups are optionally substituted with one or more substituents independently selected from $C_{1-8}$ alkyl and halogen, and any of the aryl and heteroaryl groups are optionally substituted with one or more $R_7$ groups;
each $R_5$ independently represents H or $C_{1-8}$ alkyl;
each $R_6$ independently represents $C_{1-8}$ alkyl, halogen, hydroxy$C_{0-6}$ alkyl, $C_{3-10}$ cycloalkyl optionally substituted with one or more $C_{1-8}$ alkyl groups, or phenyl optionally substituted with one or more $R_8$; and optionally two $R_6$ groups on the same carbon atom are bonded together to form a —$C_{2-5}$ alkylene- group which is optionally substituted with one or more $C_{1-8}$ alkyl groups;
each $R_7$ independently represents $C_{1-8}$ alkyl, halo$C_{1-6}$ alkyl, halogen, $C_{1-6}$ alkoxy, halo$C_{1-6}$ alkoxy$C_{1-6}$ alkylthio, $C_{2-4}$ alkynyl, hydroxy$C_{0-6}$ alkyl, $CO_2R_9$—$C_{0-6}$ alkyl, $C_{3-10}$ cycloalkyl, heterocycloalkyl, aryl or heteroaryl; wherein any of the cycloalkyl, heterocycloalkyl, aryl or heteroaryl groups in $R_7$ are optionally substituted with one or more $C_{1-8}$ alkyl groups;
each $R_8$ independently represents $C_{1-8}$ alkyl, halo$C_{1-6}$ alkyl, halogen, $C_{1-6}$ alkoxy, halo$C_{1-6}$ alkoxy or —CN, and
each $R_9$ independently represents H or $C_{1-8}$ alkyl, and n represents 1 or 2, and at least one pharmaceutically acceptable excipient.

18. A method of treating a medical condition selected from the group consisting of asthma, allergic rhinitis, dermatitis, psoriasis, urticaria, pemphigus, pruritus, and rheumatoid arthritis in a subject in need thereof comprising (i) administering to the subject a therapeutically effective amount of compound of claim 1 or a pharmaceutically acceptable salt thereof, and (ii) inhibiting the binding of histamine to $H_4$ receptor.

19. The method of claim 18, wherein the medical condition is atopic dermatitis, psoriasis, urticaria, or pemphigus.

20. The compound 4-((Cyclopropylmethylamino)methyl)-6-(3-(methylamino)azetidin-1-yl)pyrimidin-2-amine having the structure:

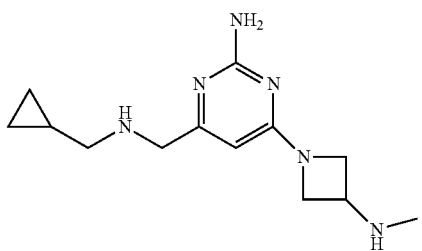 [SMILES: CNC1CN(c2cc(CNCC3CC3)nc(N)n2)C1]

or a salt thereof.

21. The compound 4-((Cyclopentylamino)methyl)-6-(3-(methylamino)azetidin-1-yl)pyrimidin-2-amine having the structure:

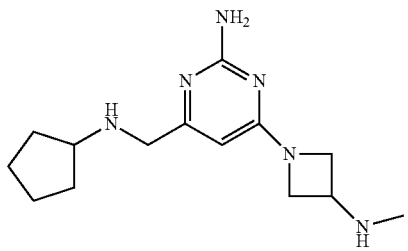 [SMILES: CNC1CN(c2cc(CNC3CCCC3)nc(N)n2)C1]

or a salt thereof.

* * * * *